(12) United States Patent
Odermatt et al.

(10) Patent No.: US 10,881,464 B2
(45) Date of Patent: Jan. 5, 2021

(54) LOWER EXTREMITIES LEG LENGTH CALCULATION METHOD

(71) Applicant: MAKO Surgical Corp., Fort Lauderdale, FL (US)

(72) Inventors: Daniel Odermatt, Fort Lauderdale, FL (US); Matt Thompson, Fort Lauderdale, FL (US)

(73) Assignee: MAKO Surgical Corp., Fort Lauderdale, FL (US)

( * ) Notice: Subject to any disclaimer, the term of this patent is extended or adjusted under 35 U.S.C. 154(b) by 362 days.

(21) Appl. No.: 15/743,625

(22) PCT Filed: Jul. 13, 2016

(86) PCT No.: PCT/US2016/042129
§ 371 (c)(1),
(2) Date: Jan. 10, 2018

(87) PCT Pub. No.: WO2017/011576
PCT Pub. Date: Jan. 19, 2017

(65) Prior Publication Data
US 2018/0199995 A1    Jul. 19, 2018

Related U.S. Application Data

(60) Provisional application No. 62/191,890, filed on Jul. 13, 2015.

(51) Int. Cl.
*A61B 34/10*     (2016.01)
*A61B 5/055*     (2006.01)
(Continued)

(52) U.S. Cl.
CPC .............. *A61B 34/10* (2016.02); *A61B 5/055* (2013.01); *A61B 5/107* (2013.01); *A61B 6/032* (2013.01);
(Continued)

(58) Field of Classification Search
CPC ......... A61B 34/10; A61B 34/20; A61B 34/25; A61B 34/30; A61B 90/50; A61B 5/055; A61B 5/107; A61B 8/00
(Continued)

(56) References Cited

U.S. PATENT DOCUMENTS 7,885,705 B2 *  2/2011  Murphy ................. A61B 90/39
                                                       600/426
7,955,280 B2 *  6/2011  Radinsky ............. A61B 5/4504
                                                       600/595
(Continued)

OTHER PUBLICATIONS

Hofmann et al. (Minimizing Leg-Length Inequality in Total Hip Arthroplasty: Use of Preoperative Templating and an Intraoperative X-Ray, 2008, American journal of orthopedics) (Year: 2008).*
(Continued)

*Primary Examiner* — Iftekhar A Khan
(74) *Attorney, Agent, or Firm* — Polsinelli PC

(57) ABSTRACT

A method of calculating leg length discrepancy of a patient including: receiving patient bone data associated with a lower body of the patient; identifying anatomical landmarks in the patient bone data; orienting a first proximal landmark and a second proximal landmark relative to each other and an origin in a coordinate system; aligning a first axis associated with a first femur and a second axis associated with a second femur with a longitudinal axis extending in a distal-proximal direction, wherein the first and second distal landmarks are adjusted according to the alignment of the first and second axes; calculating a distance between the first and second distal landmarks in the distal-proximal direction along the longitudinal axis; and displaying at least one of the distance or a portion of the patient bone data on a display screen.

7 Claims, 17 Drawing Sheets

(51) Int. Cl.

| | | |
|---|---|---|
| *A61B 5/107* | (2006.01) | |
| *A61B 6/03* | (2006.01) | |
| *A61B 6/00* | (2006.01) | |
| *A61B 34/00* | (2016.01) | |
| *A61B 34/30* | (2016.01) | |
| *A61B 8/00* | (2006.01) | |
| *A61B 34/20* | (2016.01) | |
| *A61B 90/50* | (2016.01) | |
| *A61B 8/08* | (2006.01) | |
| *A61B 17/16* | (2006.01) | |

(52) U.S. Cl.
CPC ............ *A61B 6/505* (2013.01); *A61B 6/5217* (2013.01); *A61B 8/00* (2013.01); *A61B 34/20* (2016.02); *A61B 34/25* (2016.02); *A61B 34/30* (2016.02); *A61B 90/50* (2016.02); *A61B 8/0875* (2013.01); *A61B 8/5223* (2013.01); *A61B 17/1666* (2013.01); *A61B 2034/101* (2016.02); *A61B 2034/104* (2016.02); *A61B 2034/105* (2016.02); *A61B 2034/108* (2016.02)

(58) Field of Classification Search
USPC .......................................................... 703/1
See application file for complete search history.

(56) References Cited

U.S. PATENT DOCUMENTS

| | | | | |
|---|---|---|---|---|
| 8,010,180 B2* | 8/2011 | Quaid | ................... | A61N 1/0534 600/424 |
| 8,092,465 B2* | 1/2012 | Metzger | ................ | A61B 17/56 606/96 |
| 8,737,700 B2* | 5/2014 | Park | ....................... | B33Y 50/00 382/128 |
| 9,307,929 B2* | 4/2016 | Colwell, Jr. | ........ | A61B 17/1671 |
| 9,445,909 B2* | 9/2016 | Cohen | .................... | A61F 2/389 |
| 9,532,845 B1* | 1/2017 | Dossett | ................. | A61B 34/25 |
| 10,363,149 B2* | 7/2019 | van der Walt | ..... | A61B 17/1746 |
| 10,485,450 B2* | 11/2019 | Gupta | .................... | A61B 34/30 |
| 2004/0111909 A1* | 6/2004 | Pourmanafzadeh | ....................... A61B 5/1072 33/512 | |
| 2004/0133276 A1* | 7/2004 | Lang | ................... | A61F 2/30756 623/14.12 |
| 2004/0230199 A1* | 11/2004 | Jansen | ................ | A61B 17/175 606/91 |
| 2006/0122541 A1* | 6/2006 | Tuma | .................. | A61B 5/4528 600/587 |
| 2006/0142657 A1* | 6/2006 | Quaid | ................. | A61B 17/1764 600/424 |
| 2006/0189864 A1* | 8/2006 | Paradis | .................. | A61B 34/20 600/407 |
| 2006/0264731 A1* | 11/2006 | Murphy | ................ | A61B 90/36 600/407 |
| 2006/0293614 A1* | 12/2006 | Radinsky | ............. | A61B 5/4504 600/587 |
| 2007/0173815 A1* | 7/2007 | Murase | ................... | G06F 19/00 606/53 |
| 2007/0179626 A1* | 8/2007 | de la Barrera | ......... | A61B 34/10 623/20.14 |
| 2007/0198022 A1* | 8/2007 | Lang | ........................ | A61F 2/38 606/88 |
| 2008/0004633 A1* | 1/2008 | Arata | ................. | A61B 17/1764 606/130 |
| 2008/0033442 A1* | 2/2008 | Amiot | ................. | A61B 5/1077 606/80 |
| 2008/0146969 A1* | 6/2008 | Kurtz | .................... | A61B 17/56 600/595 |
| 2008/0243127 A1* | 10/2008 | Lang | .................... | A61B 17/155 606/87 |
| 2008/0312659 A1* | 12/2008 | Metzger | ................. | G06Q 50/24 606/87 |
| 2008/0319449 A1* | 12/2008 | Tuma | ...................... | A61B 90/36 606/102 |
| 2009/0125117 A1* | 5/2009 | Paradis | ................ | A61B 5/4528 623/22.11 |
| 2011/0029116 A1* | 2/2011 | Jordan | ................ | A61B 17/157 700/98 |
| 2011/0082468 A1* | 4/2011 | Hagag | ..................... | A61B 34/20 606/130 |
| 2011/0092858 A1* | 4/2011 | Burger | ..................... | A61B 34/10 600/587 |
| 2011/0295378 A1* | 12/2011 | Bojarski | ................... | A61F 2/30 623/20.35 |
| 2012/0041446 A1* | 2/2012 | Wong | ..................... | A61F 2/3859 606/96 |
| 2012/0209394 A1* | 8/2012 | Bojarski | .............. | A61B 17/157 623/20.32 |
| 2013/0072821 A1* | 3/2013 | Odermatt | ............... | A61B 34/25 600/595 |
| 2013/0197526 A1* | 8/2013 | Park | ....................... | A61B 6/032 606/87 |
| 2013/0204382 A1* | 8/2013 | Walker | ...................... | A61F 2/38 623/20.31 |
| 2013/0211531 A1* | 8/2013 | Steines | .................. | A61F 2/3859 623/20.35 |
| 2014/0188240 A1* | 7/2014 | Lang | ..................... | A61F 2/3609 623/22.12 |
| 2014/0208578 A1* | 7/2014 | Linderman | .......... | A61B 17/155 29/592 |
| 2014/0316526 A1* | 10/2014 | Grotz | ..................... | A61F 2/3859 623/20.17 |
| 2014/0330281 A1* | 11/2014 | Aghazadeh | ........... | A61B 17/58 606/102 |
| 2015/0018719 A1* | 1/2015 | Aghazadeh | .......... | A61B 5/6878 600/587 |
| 2015/0032215 A1* | 1/2015 | Slamin | ................ | A61F 2/30942 623/20.21 |
| 2015/0057756 A1* | 2/2015 | Lang | ....................... | A61F 2/389 623/20.15 |
| 2015/0164728 A1* | 6/2015 | Kreuzer | ................. | A61G 7/075 5/624 |
| 2016/0008143 A1* | 1/2016 | Mahfouz | ................ | A61F 2/461 606/102 |
| 2016/0220391 A1* | 8/2016 | Duval | .................. | A61B 5/1079 |
| 2016/0331467 A1* | 11/2016 | Slamin | ................ | A61F 2/30756 |
| 2017/0325892 A1* | 11/2017 | Aghazadeh | ............ | A61F 2/34 |
| 2018/0235641 A1* | 8/2018 | McAuliffe | ........... | A61B 17/154 |

OTHER PUBLICATIONS

Ogawa et al. (Accurate Leg Length Measurement in Total Hip Arthroplasty: A Comparison of Computer Navigation and a Simple Manual Measurement Device, 2014, The Korean Orthopaedic Association) (Year: 2014).*

Subotnic et al . ("Limb Length Discrepancies of the Lower Extremity (The Short Leg Syndrome)", JOSPT, 1981, pp. 11-16) (Year: 1981).*

Woerman et al. ("Leg Length Discrepancy Assessment: Accuracy and Precision in Five Clinical methods off Evaluation",JOSPT, 1984, pp. 230-239) (Year: 1984).*

Sabharwal et al. ("Methods for Assessing Leg Length Discrepancy", Clin Orthop Relat Res (2008) pp. 2910-2922) (Year: 2008).*

* cited by examiner

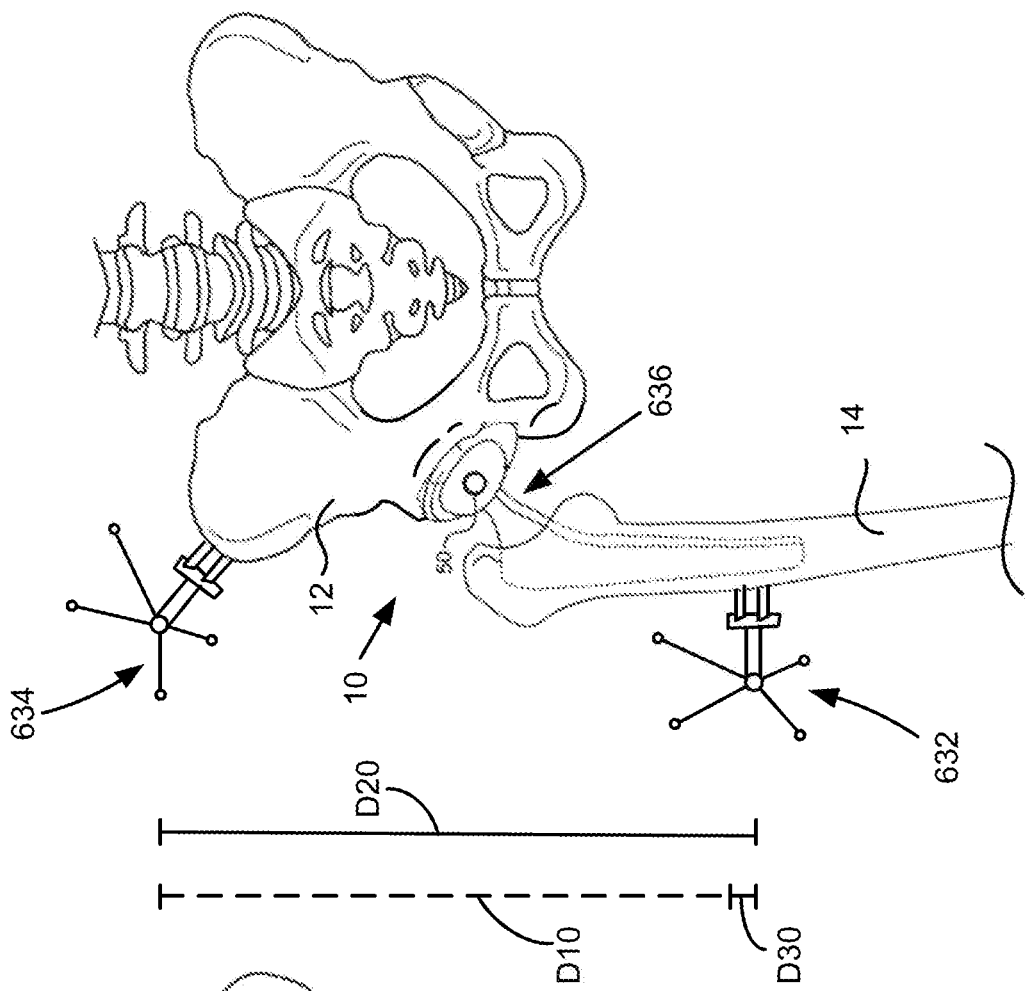
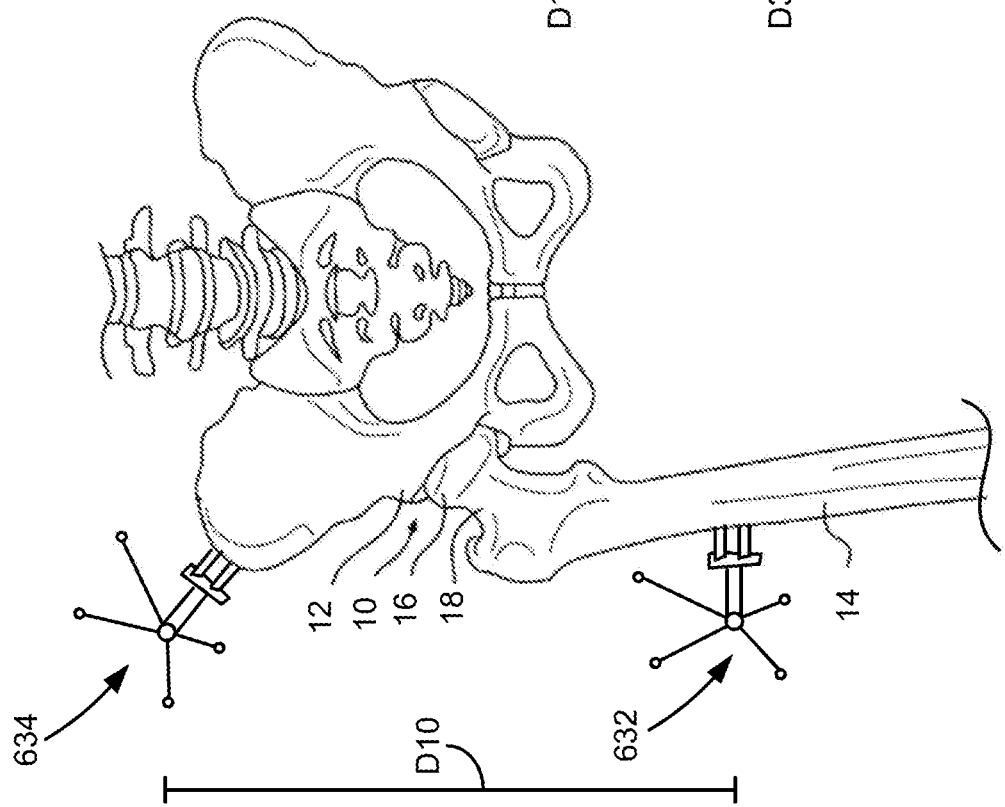

LOWER EXTREMITIES LEG LENGTH CALCULATION METHOD

CROSS-REFERENCE TO RELATED APPLICATIONS

This applications claims priority to and the benefit of U.S. Provisional Patent Application No. 62/191,890, filed Jul. 13, 2015, entitled "LOWER EXTREMITIES LEG LENGTH CALCULATION METHOD", which is hereby incorporated by reference in its entirety.

This application incorporates by reference the following applications in their entireties: U.S. patent application Ser. No. 12/894,071, filed Sep. 29, 2010, entitled "SURGICAL SYSTEM FOR POSITIONING PROSTHETIC COMPONENT AND/OR FOR CONSTRAINING MOVEMENT OF SURGICAL TOOL"; U.S. patent application Ser. No. 13/234,190, filed Sep. 16, 2011, entitled "SYSTEMS AND METHOD FOR MEASURING PARAMETERS IN JOINT REPLACEMENT SURGERY"; U.S. patent application Ser. No. 11/357,197, filed Feb. 21, 2006, entitled "HAPTIC GUIDANCE SYSTEM AND METHOD"; U.S. patent application Ser. No. 12/654,519, filed Dec. 22, 2009, entitled "TRANSMISSION WITH FIRST AND SECOND TRANSMISSION ELEMENTS"; U.S. patent application Ser. No. 12/644,964, filed Dec. 22, 2009, entitled "DEVICE THAT CAN BE ASSEMBLED BY COUPLING"; and U.S. patent application Ser. No. 11/750,807, filed May 18, 2007, entitled "SYSTEM AND METHOD FOR VERIFYING CALIBRATION OF A SURGICAL DEVICE".

TECHNICAL FIELD

The present disclosure relates generally to surgical methods used in orthopedic joint replacement surgery and, more particularly, to methods of lower extremities leg length calculations.

BACKGROUND

Robotic systems are often used in applications that require a high degree of accuracy and/or precision, such as surgical procedures or other complex tasks. Such systems may include various types of robots, such as autonomous, tele-operated, and interactive.

Interactive robotic systems may be preferred for some types of surgery, such as joint replacement surgery, because they enable a surgeon to maintain direct, hands-on control of the surgical procedure while still achieving a high degree of accuracy and/or precision. For example, in knee replacement surgery, a surgeon can use an interactive, haptically guided robotic arm in a passive manner to sculpt bone to receive a joint implant, such as a knee implant. To sculpt bone, the surgeon manually grasps and manipulates the robotic arm to move a cutting tool (e.g., a rotating burr) that is coupled to the robotic arm to cut a pocket in the bone. As long as the surgeon maintains a tip of the burr within a predefined virtual cutting boundary or haptic boundary defined, for example, by a haptic object, the robotic arm moves freely with low friction and low inertia such that the surgeon perceives the robotic arm as essentially weightless and can move the robotic arm as desired. If the surgeon attempts to move the tip of the burr to cut outside the virtual cutting boundary, however, the robotic arm provides haptic feedback (e.g., forced resistance) that prevents or inhibits the surgeon from moving the tip of the burr beyond the virtual cutting boundary. In this manner, the robotic arm enables highly accurate, repeatable bone cuts. When the surgeon manually implants a knee implant (e.g., a patellofemoral component) on a corresponding bone cut the implant will generally be accurately aligned due to the configuration of and interface between the cut bone and the knee implant.

The above-described interactive robotic system may also be used in hip replacement surgery, which may require the use of multiple surgical tools having different functions (e.g., reaming, impacting), different configurations (e.g., straight, offset), and different weights. A system designed to accommodate a variety of tools is described in U.S. patent application Ser. No. 12/894,071, filed Sep. 29, 2010, entitled "SURGICAL SYSTEM FOR POSITIONING PROSTHETIC COMPONENT AND/OR FOR CONSTRAINING MOVEMENT OF SURGICAL TOOL", which is hereby incorporated by reference in its entirety.

During a hip replacement surgery, as well as other robotically assisted or fully autonomous surgical procedures, the patient bone is intra-operatively registered with a corresponding virtual or computer bone model to correlate the pose (i.e., position and rotational orientation) of the actual, physical bone with the virtual bone model. The patient bone (physical space) is also tracked relative to the surgical robot, haptic device, or surgical tool with at least one degree of freedom (e.g., rotating burr). In this way, the virtual cutting or haptic boundaries controlled and defined on the virtual bone model via a computer can be applied to the patient bone (physical space) such that the haptic device is constrained in its physical movement (e.g., burring) when working on the patient bone (physical space).

During a hip replacement procedure, a surgeon may attempt to correct a patient's leg length discrepancy (LLD), which is a difference in the length of the right and left leg, either caused by a true length discrepancy of one or more bones or a misalignment of one or more joints. The use of an accurate and reliable algorithm to assess LLD before and during surgery is important for planning and executing precision total hip replacement. Conventional imaging methods for measuring LLD involve measuring the distance between a pelvic reference (e.g., inter-ischial, tear drop line) and another reference on the proximal or distal femurs. Other conventional methods involve using tape measures and standing blocks to asses LLD pre or post-operatively. Intra-operatively, LLD is typically measured manually by palpating the distal femurs or malleoli with the patient supine and the legs in line with the shoulders. Most of these methods have limitations and may not provide reliable measurements of LLD. Thus, there is an opportunity to use pre-operative imaging such as but not limited to computed tomography (CT) data from the pelvis, knees and lower extremities to develop a reliable, repeatable algorithm for LLD measurement that accounts for the full length of the leg.

SUMMARY

Aspects of the present disclosure involve a method of calculating leg length discrepancy of a patient. In certain instances, the method may include receiving patient bone data associated with a lower body of the patient, the lower body includes a first side and a second side, the first side includes a first portion of a pelvis, a first femur, a first tibia, and a first distal extremity, the second side includes a second portion of the pelvis, a second femur, a second tibia, and a second distal extremity. In certain instances, the method may further include identifying anatomical landmarks in the patient bone data, the anatomical landmarks includes a first proximal landmark and a first distal landmark associated with the first side and a second proximal landmark and a second distal landmark associated with the second side. In certain instances, the method may further include orienting the first proximal landmark and the second proximal landmark relative to each other and an origin in a coordinate system. In certain instances, the method may further include aligning a first axis associated with the first femur and a second axis associated with the second femur with a longitudinal axis extending in a distal-proximal direction, the first and second distal landmarks may be adjusted according to the alignment of the first and second axes. In certain instances, the method may further include calculating the leg length discrepancy based on a first distance between the first proximal landmark and the first distal landmark and a second distance between the second proximal landmark and the second distal landmark. In certain instances, the method may further include displaying at least one of the leg length discrepancy or a portion of the patient bone data on a display screen.

In certain instances, the first axis may include a first femoral mechanical axis, and the second axis may include a second femoral mechanical axis.

In certain instances, the first axis and the second axis may be aligned parallel to the longitudinal axis.

In certain instances, the first and second proximal landmarks remain in an unchanged orientation relative to the origin when the first and second axes are aligned relative to the longitudinal axis.

In certain instances, the longitudinal axis may be defined as a normal vector to a pelvic axis extending through the first and second proximal landmarks.

In certain instances, the first proximal landmark may be associated with a first location on the first portion of the pelvis, and the second proximal landmark may be associated with a second location on the second portion of the pelvis.

In certain instances, the first tibia and the first distal extremity have a first alignment relative to the first femur that may be unchanged when the first and second axes may be aligned, the second tibia and the second distal extremity have a second alignment relative to the second femur that may be unchanged when the first and second axes may be aligned.

In certain instances, further includes adjusting at least one of the first alignment or the second alignment so as to adjust a condition at a knee joint.

In certain instances, the condition may be a valgus or valrus deformity.

In certain instances, the condition may be a flexed or extended knee joint.

In certain instances, further includes generating a three dimensional bone model of the first side and the second side from the patient bone data.

In certain instances, the patient bone data may include medical images of the lower body of the patient.

In certain instances, the medical images were generated from a medical imaging machine includes at least one of a CT scanner, MRI machine, ultrasound scanner, or X-ray machine.

In certain instances, the patient bone data may be captured via at least one of an intra-operative bone scanner, a digitizer, or a navigated ultrasound probe.

In certain instances, the first distal extremity may be a first talus bone, and the second distal extremity may be a second talus bone.

In certain instances, calculating the leg length discrepancy may include determining a difference between the first and second distances in the distal-proximal direction.

In certain instances, calculating the leg length discrepancy may include determining a distance between the first and second distal landmarks in the distal-proximal direction.

Aspects of the present disclosure involve a method of calculating leg length discrepancy of a patient body including a first side and a second side, the first side including a first portion of a pelvis, a first femur, a first tibia, and a first foot region, the second side including a second portion of the pelvis, a second femur, a second tibia, and a second foot region. In certain instances, the method may include receiving patient bone data associated with the first and a second sides of the patient body, one of the first or second sides including a degenerate or deformed condition, the patient bone data having been generated by a medical imaging device. In certain instances, the method may further include generating a computer model of the first and second sides of the patient body from the patient bone data. In certain instances, the method may further include identifying anatomical landmarks in the patient bone data or the computer model, the anatomical landmarks includes: a first proximal point and a first distal point on the first side; and a second proximal point and a second distal point on the second side. In certain instances, the method may further include orienting the first and second sides of the computer model relative to each other in a coordinate system such that: a pelvic axis extending through the first and second proximal points may be generally perpendicular to a longitudinal axis of the first and second sides of the computer model; and a first axis associated with the first femur and a second axis associated with the second femur may be generally parallel to the longitudinal axis. In certain instances, the method may further include calculating the leg length discrepancy based on the first and second sides of the computer model after orienting the first and second sides of the computer model relative to each other. In certain instances, the method may further include displaying at least one of the leg length discrepancy or a portion of the computer model on a display screen.

In certain instances, the first proximal point corresponds to a femoral head center of the first femur, and the second proximal point corresponds to a femoral head center of the second femur.

In certain instances, the first distal point corresponds to a first point in or on a first bone in the first foot region, and the second distal point corresponds to a second point in or on a second bone in the second foot region.

In certain instance, further includes: adjusting an orientation of at least one of a first knee joint of the computer model defined between the first femur and the first tibia or a second knee joint of the computer model defined between the second femur and the second tibia.

In certain instances, the patient bone data may include at least one of CT images, MR images, or X-ray images.

In certain instances, the leg length discrepancy may include determining a distance between the first and second distal points in a direction of the longitudinal axis.

In certain instances, the leg length discrepancy may include determining a difference between a first distance and a second distance, the first distance defined between the first proximal point and the first distal point on the first side, the second distance defined between the second proximal point and the second distal point on the second side.

Aspects of the present disclosure involve a method of calculating leg length discrepancy of a lower body of a patient includes a pelvic region, femurs, tibias, and feet. In certain instances, the method may include receiving patient bone data representative of at least a portion of the lower body of the patient including the pelvic region, femurs, tibias, and feet, the patient bone data having been generated via a medical imaging device. In certain instances, the method may further include generating computer models of the lower body from the patient bone data, the computer models including first and second side pelvic models, first and second femur models, first and second tibia models, and first and second foot models. In certain instances, the method may further include orienting the first and second side pelvic models relative to an origin in a coordinate system. In certain instances, the method may further include orienting the first and second femur models, first and second tibia models, and first and second foot models relative to the first and second side pelvic models. In certain instances, the method may further include adjusting an orientation of one of the first and second femur models, first and second tibia models, or first and second foot models with respect to an anteroposterior or mediolateral axis. In certain instances, the method may further include calculating the leg length discrepancy based upon a difference in length between a first landmark in the first foot model and a second landmark in the second foot model in a direction of a longitudinal axis extending from the first and second foot models to the first and second side pelvic models. In certain instances, the method may further include displaying at least one of the difference or a portion of the computer models on a display screen.

In certain instances, the patient bone data may include at least one of CT images, MR images, or X-ray images.

In certain instances, the first landmark may be a first point in or on a talus bone of the first foot model, and the second landmark may be a second point in or on a talus bone of the second foot model.

In certain instances, the patient bone data may include information associated with a statistical bone model.

BRIEF DESCRIPTION OF THE DRAWINGS

FIG. 12A is a coronal view of a skeletal structure of a patient with a pelvic tracking array in the pelvis and a femoral tracking array in the femur prior to the resection of the femur.
FIG. 12B is a coronal view of a skeletal structure of a patient with a pelvic tracking array in the pelvis and a femoral tracking array in the femur following the resection of the femur and implantation of a femoral and acetabular component of a hip replacement system.

DETAILED DESCRIPTION

I. Overview

Figure 1A:
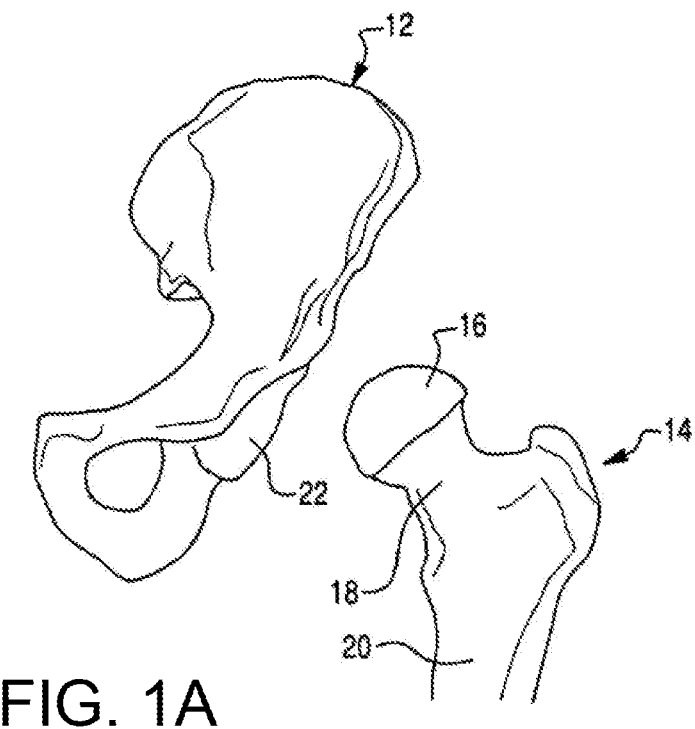
FIG. 1A is a perspective view of a femur and a pelvis.

The hip joint is the joint between the femur and the pelvis and primarily functions to support the weight of the body in static (e.g., standing) and dynamic (e.g., walking) postures. FIG. 1A illustrates the bones of a hip joint 10, which include a left pelvis 12 and a proximal end of a left femur 14. The proximal end of the femur 14 includes a femoral head 16 disposed on a femoral neck 18. The femoral neck 18 connects the femoral head 16 to a femoral shaft 20.

Figure 1B:
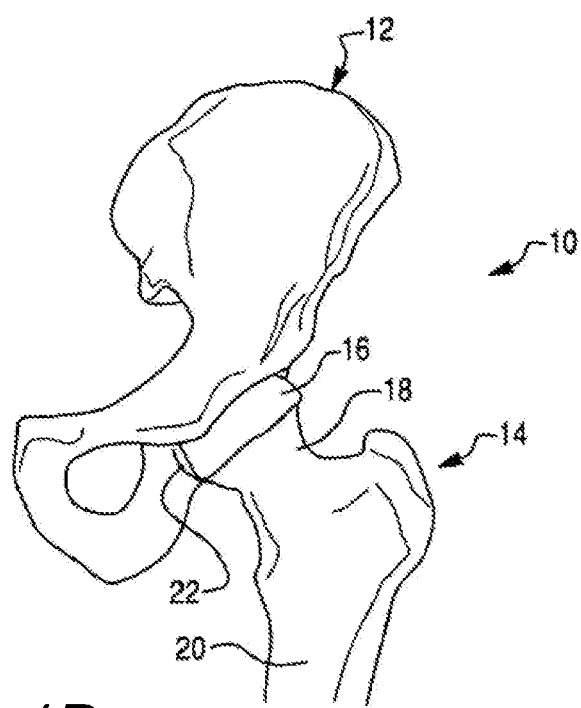
FIG. 1B is a perspective view of a hip joint formed by the femur and pelvis of FIG. 1A.
Figure 2B:
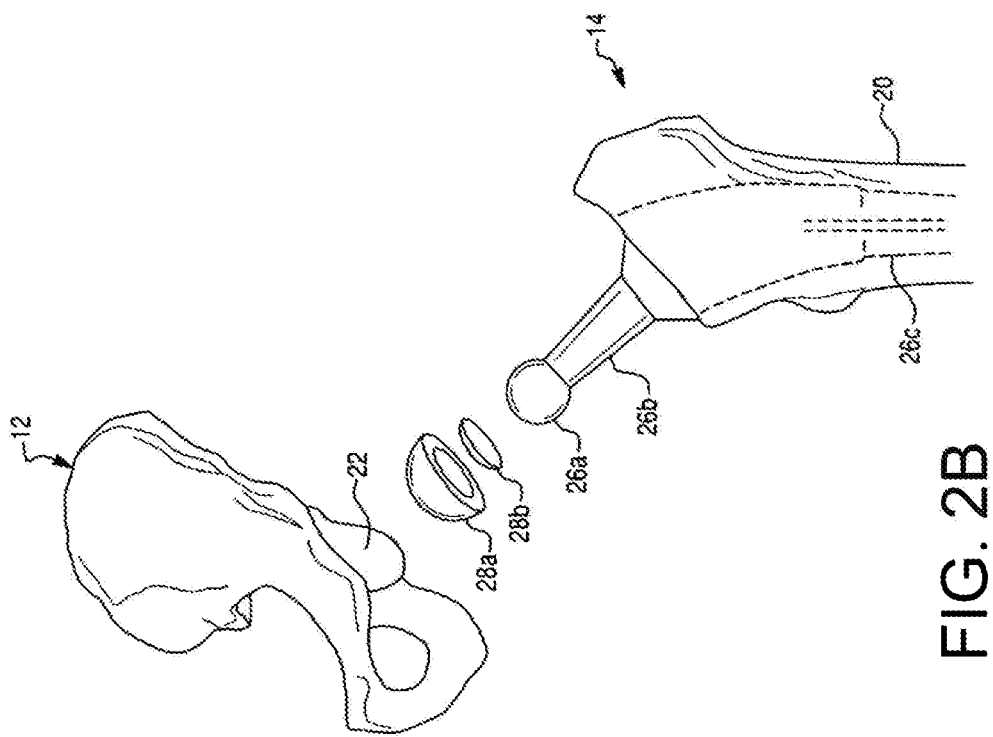
FIG. 2B is a perspective view illustrating placement of the femoral component and acetabular component of FIG. 2A in relation to the femur and pelvis of FIG. 1A, respectively.
Figure 2A:
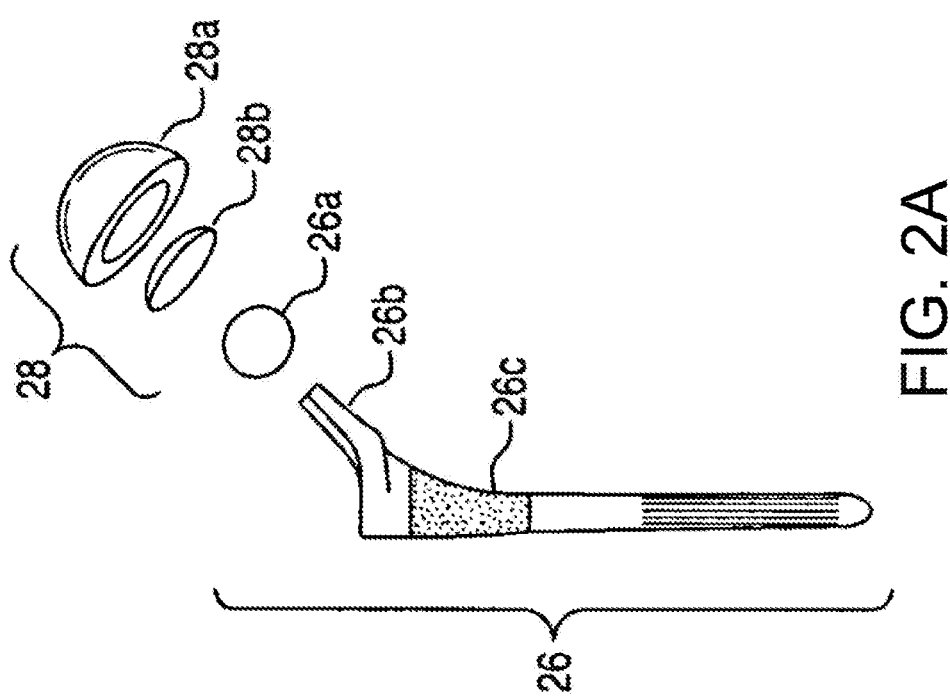
FIG. 2A is an exploded perspective view of a femoral component and an acetabular component for a total hip replacement procedure.

As shown in FIG. 1B, the femoral head 16 fits into a concave socket in the pelvis 12 called the acetabulum 22, thereby forming the hip joint 10. The acetabulum 22 and femoral head 16 are both covered by articular cartilage that absorbs shock and promotes articulation of the joint 10. Over time, the hip joint 10 may degenerate (e.g., due to osteoarthritis) resulting in pain and diminished functionality. As a result, a hip replacement procedure, such as total hip arthroplasty or hip resurfacing, may be necessary. During hip replacement, a surgeon replaces portions of a patient's hip joint 10 with artificial components. In total hip arthroplasty, the surgeon removes the femoral head 16 and neck 18 and replaces the natural bone with a prosthetic femoral component 26 comprising a head 26a, a neck 26b, and a stem 26c (shown in FIG. 2A). As shown in FIG. 2B, the stem 26c of the femoral component 26 is anchored in a cavity the surgeon creates in the intramedullary canal of the femur 14. Alternatively, if disease is confined to the surface of the femoral head 16, the surgeon may opt for a less invasive approach in which the femoral head is resurfaced (e.g., using a cylindrical reamer) and then mated with a prosthetic femoral head cup (not shown). Similarly, if the natural acetabulum 22 of the pelvis 12 is worn or diseased, the surgeon resurfaces the acetabulum 22 using a reamer and replaces the natural surface with a prosthetic acetabular component 28 comprising a hemispherical shaped cup 28a (shown in FIG. 2A) that may include a liner 28b. To install the acetabular component 28, the surgeon connects the cup 28a to a distal end of an impactor tool and implants the cup 28a into the reamed acetabulum 22 by repeatedly striking a proximal end of the impactor tool with a mallet. If the acetabular component 28 includes a liner 28b, the surgeon snaps the liner 28b into the cup 28a after implanting the cup 28a. Depending on the position in which the surgeon places the patient for surgery, the surgeon may use a straight or offset reamer to ream the acetabulum 22 and a straight or offset impactor to implant the acetabular cup 28a. For example, a surgeon that uses a postero-lateral approach may prefer straight reaming and impaction whereas a surgeon that uses an antero-lateral approach may prefer offset reaming and impaction.

II. Exemplary Robotic System

Figure 3A:
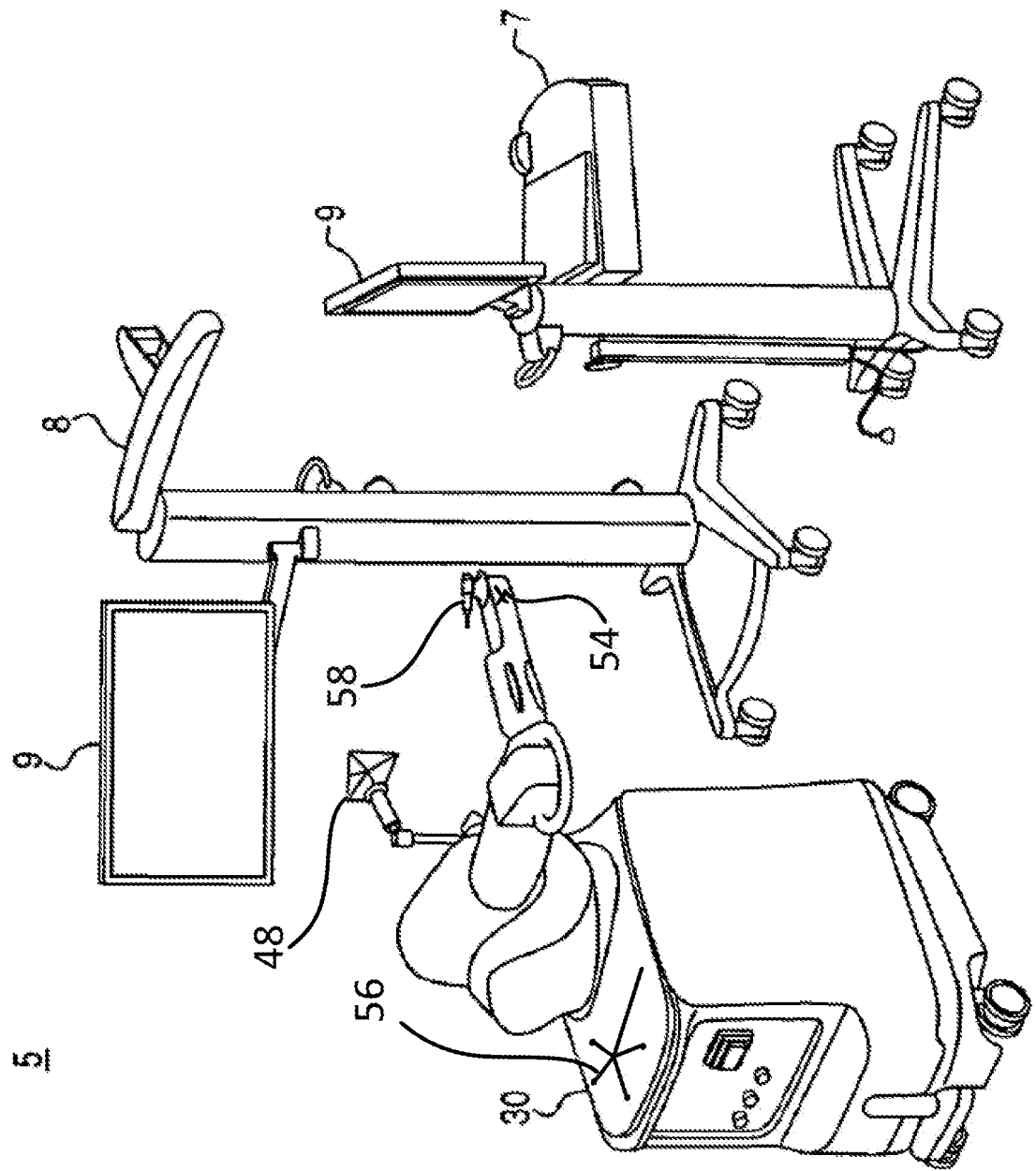
FIG. 3A is a perspective view of an embodiment of a surgical system.

A surgical system described herein may be utilized to perform hip replacement, as well as other surgical procedures. As shown in FIG. 3A, an embodiment of a surgical system 5 for surgical applications according to the present disclosure includes a computer assisted navigation system 7, a tracking device 8, a computer 15, a display device 9 (or multiple display devices 9), and a robotic arm 30.

Figure 3B:
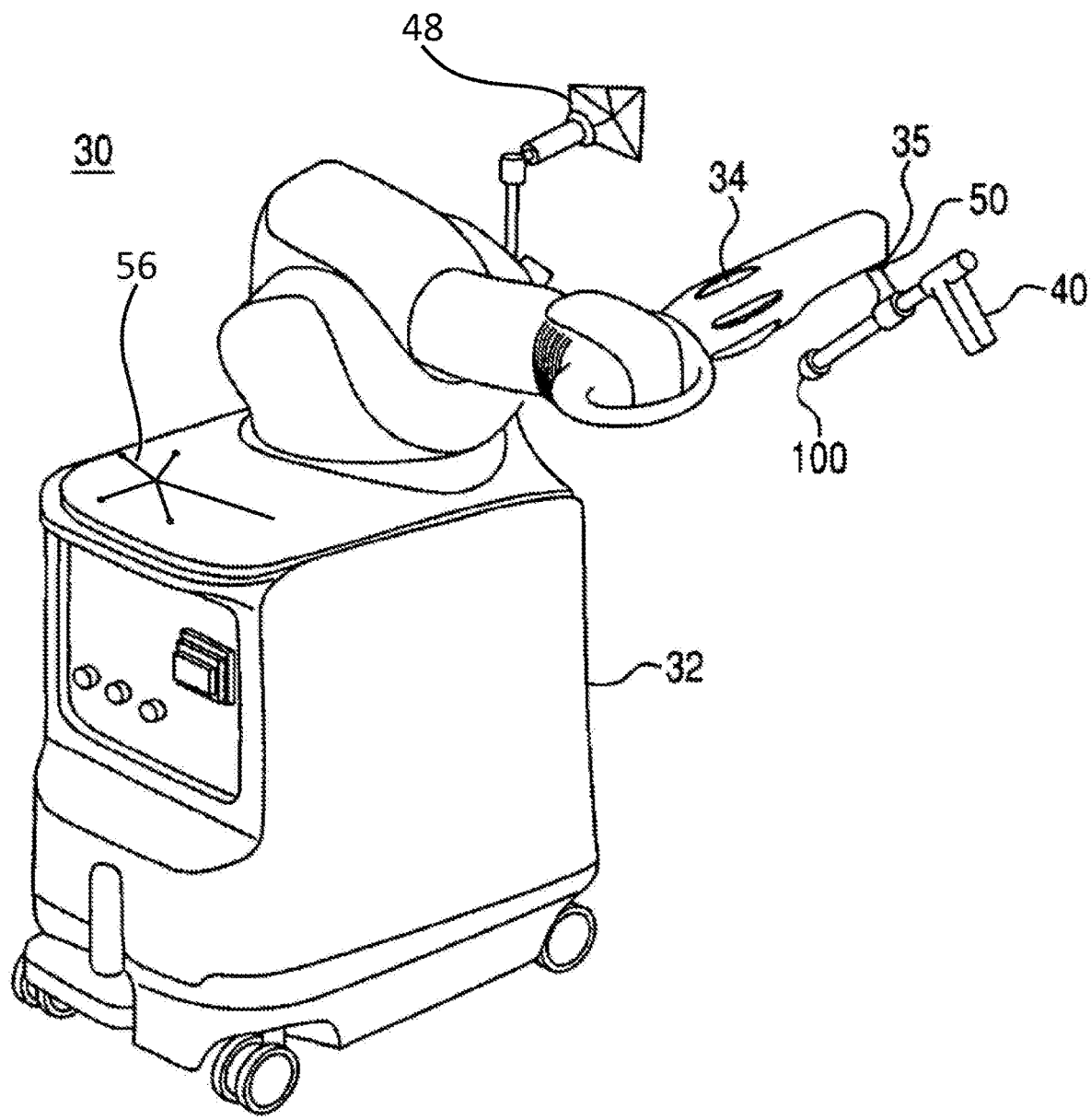
FIG. 3B is a perspective view of an embodiment of a robotic arm of the surgical system of FIG. 3A.

The robotic arm 30 can be used in an interactive manner by a surgeon to perform a surgical procedure on a patient, such as a hip replacement procedure. As shown in FIG. 3B, the robotic arm 30 includes a base 32, an articulated arm 34, a force system (not shown), and a controller (not shown). A surgical tool 58 (e.g., a rotary burring device as seen in FIG. 3A, an end effector 40 having an operating member as seen in FIG. 3B) is coupled to an end of the articulated arm 34, and the surgeon manipulates the surgical tool 58 by grasping and manually moving the articulated arm 34 and/or the surgical tool.

The force system and controller are configured to provide control or guidance to the surgeon during manipulation of the surgical tool. The force system is configured to provide at least some force to the surgical tool via the articulated arm 34, and the controller is programmed to generate control signals for controlling the force system. In one embodiment, the force system includes actuators and a backdriveable transmission that provide haptic (or force) feedback to constrain or inhibit the surgeon from manually moving the surgical tool beyond predefined virtual boundaries defined by haptic objects as described, for example, in U.S. patent application Ser. No. 11/357,197 (Pub. No. US 2006/0142657), filed Feb. 21, 2006, and/or U.S. patent application Ser. No. 12/654,519, filed Dec. 22, 2009, each of which is hereby incorporated by reference herein in its entirety. In a certain embodiment the surgical system is the RIO®. Robotic Arm Interactive Orthopedic System manufactured by MAKO Surgical Corp. of Fort Lauderdale, Fla. The force system and controller are preferably housed within the robotic arm 30.

The tracking device 8 is configured to track the relative locations of the surgical tool 58 (coupled to the robotic arm 30) and the patient's anatomy. The surgical tool 58 can be tracked directly by the tracking device 8. Alternatively, the pose of the surgical tool can be determined by tracking the location of the base 32 of the robotic arm 30 and calculating the pose of the surgical tool 58 based on joint encoder data from joints of the robotic arm 30 and a known geometric relationship between the surgical tool and the robotic arm 30. In particular, the tracking device 8 (e.g., an optical, mechanical, electromagnetic, or other known tracking system) tracks (or enables determination of) the pose (i.e., position and orientation) of the surgical tool and the patient's anatomy so the navigation system 7 knows the relative relationship between the tool and the anatomy.

In operation, a user (e.g., a surgeon) manually moves the robotic arm 30 to manipulate the surgical tool 58 (e.g., the rotary burring device, the end effector 40 having an operating member) to perform a surgical task on the patient, such as bone cutting or implant installation. As the surgeon manipulates the tool 58, the tracking device 8 tracks the location of the surgical tool and the robotic arm 30 provides haptic (or force) feedback to limit the surgeon's ability to move the tool 58 beyond a predefined virtual boundary that is registered (or mapped) to the patient's anatomy, which results in highly accurate and repeatable bone cuts and/or implant placement. The robotic arm 30 operates in a passive manner and provides haptic feedback when the surgeon attempts to move the surgical tool 58 beyond the virtual boundary. The haptic feedback is generated by one or more actuators (e.g., motors) in the robotic arm 30 and transmitted to the surgeon via a flexible transmission, such as a cable drive transmission. When the robotic arm 30 is not providing haptic feedback, the robotic arm 30 is freely moveable by the surgeon and preferably includes a virtual brake that can be activated as desired by the surgeon. During the surgical procedure, the navigation system 7 displays images related to the surgical procedure on one or both of the display devices 9.

To aid in tracking the various pieces of equipment within the system, the robotic arm 30 may include a device marker 48 to track a global or gross position of the robotic arm 30, a tool end marker 54 to track the distal end of the articulating arm 34, and a free-hand navigation probe 56 for use in the registration process. Each of these markers 48, 54, 56 (among others such as navigation markers positioned in the patient's bone) is trackable by the tracking device 8 with optical cameras, for example.

The computer 15 may include a display and an input device (e.g., keyboard, mouse) and is configured to communicate with the navigation system 7, the tracking device 8, the various display devices 9 in the system, and the robotic arm 30. Furthermore, the computer 15 may receive information related to a particular surgical procedure and perform various functions related to performance of the surgical procedure. For example, the computer 15 may have software as necessary to perform functions related to image analysis, surgical planning, registration, navigation, image guidance, and haptic guidance. A more detailed analysis of an example computing system having one or more computing units that may implement various systems and methods discussed herein, is described subsequently in reference to FIG. 14.

FIG. 3B depicts an end effector 40 particularly suited for use in robotic assisted hip arthroplasty. The end effector 40 is configured to be mounted to an end of the robotic arm 30. The end effector 40 includes a mounting portion 50, a housing, a coupling device, and a release member. The end effector 40 is configured to individually and interchangeably support and accurately position multiple operating members relative to the robotic arm 30. As seen in FIG. 3B, the end effector 40 is coupled to an operating member 100. The end effector 40 and related tools, systems, and methods are described in U.S. patent application Ser. No. 12/894,071, filed Sep. 29, 2010, which is hereby incorporated by reference in its entirety.

The mounting portion (or mount) 50 preferably couples the end effector 40 to the robotic arm 30. In particular, the mounting portion 50 extends from the housing and is configured to couple the end effector 40 to a corresponding mounting portion 35 of the robotic arm 30 using, for example, mechanical fasteners, such that the mounting portions are fixed relative to one another. The mounting portion 50 can be attached to the housing or formed integrally with the housing and is configured to accurately and repeatably position the end effector 40 relative to the robotic arm 30. In one embodiment, the mounting portion 50 is a semi-kinematic mount as described in U.S. patent application Ser. No. 12/644,964, filed Dec. 22, 2009, and hereby incorporated by reference herein in its entirety.

The end effector 40 in FIG. 3B is one example of a surgical tool that can be tracked and used by the surgical robotic arm 30. Other tools (e.g., drills, burrs) as known in the art can be attached to the robotic arm for a given surgical procedure.

III. Pre-operative Planning a Surgical Procedure

Figure 4:
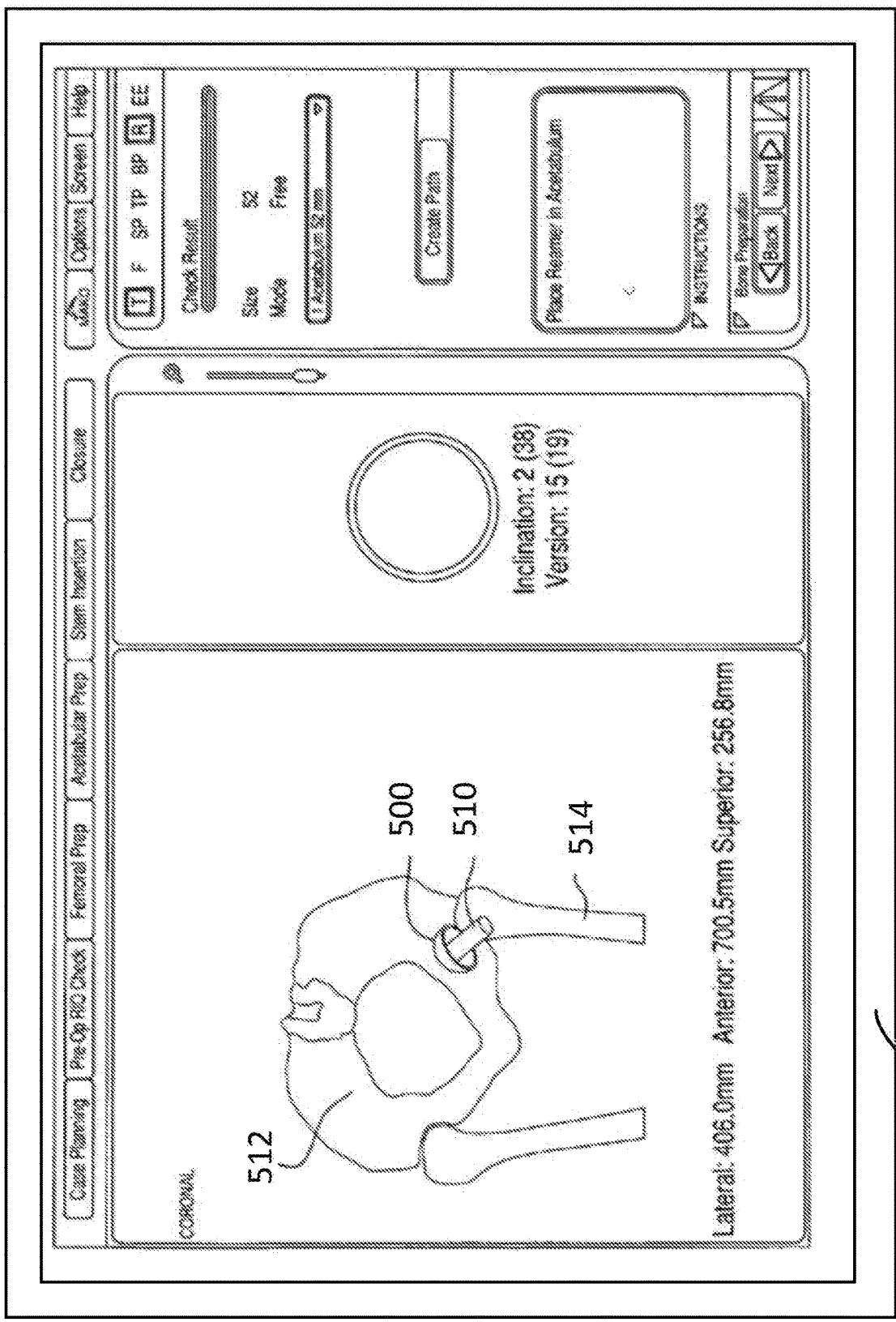
FIG. 4 illustrates an embodiment of a computer display for use during a surgical procedure.
Figure 5A:
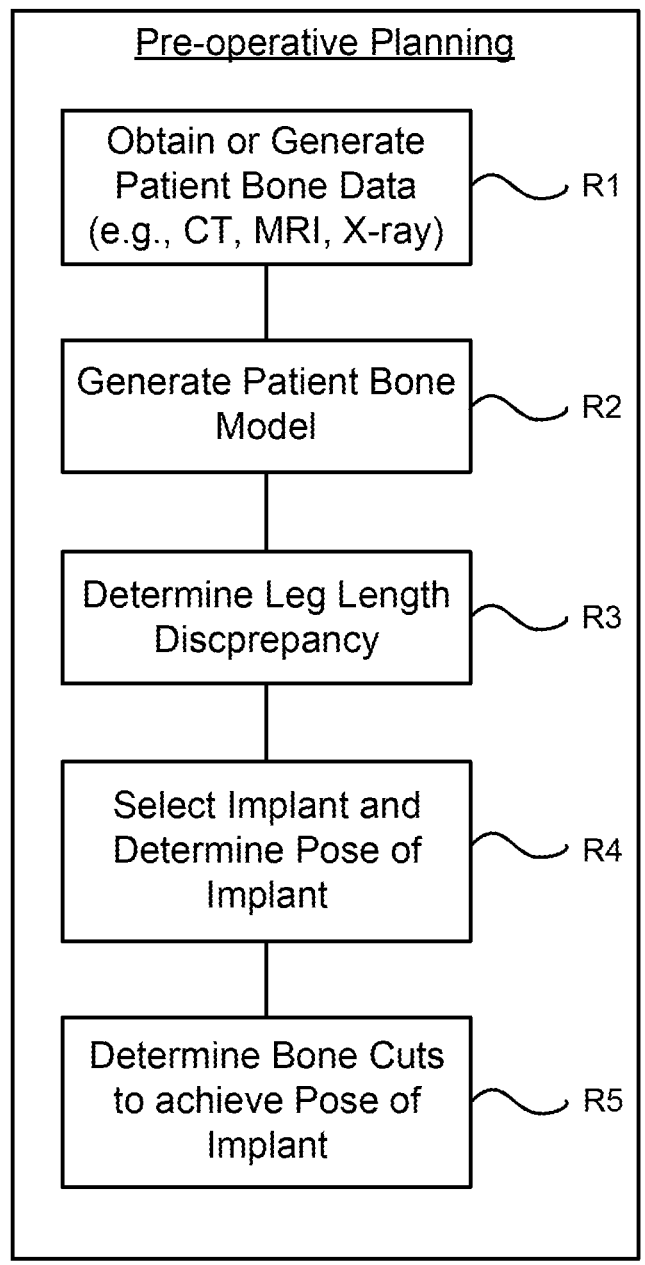
FIG. 5A illustrates an embodiment of steps of pre-operatively planning a hip replacement procedure.

Referring to FIGS. 4 and 5A, a preoperative CT (computed tomography) scan of the patient's pelvis 12 and femur 14 is generated or obtained at step R1. The scan image may be generally described as "patient data" or "patient bone data." Such patient data may be generated with a medical imaging device (e.g., CT scanner) prior to the surgical procedure. While the discussion will focus on CT scans, other imaging modalities (e.g., MRI) may be similarly be employed. Additionally and alternatively, X-ray images derived from the CT scan and/or the three dimensional models 512, 514 can be used for surgical planning, which may be helpful to surgeons who are accustomed to planning implant placement using actual X-ray images as opposed to CT based models. The CT scan may be performed by the surgeon or at an independent imaging facility. Additionally or alternatively, intra-operative imaging methods may be employed to generate a patient model of the bone. For example, various boney surfaces of interest may be probed with a tracked probe to generate a surface profile of the surface of interest. The surface profile may be used as the patient bone model. Additionally and alternatively, generic bone data or models (e.g., based on statistical averages of a sample population) that are at least partially representative of the patient's bone shape and lengths, among other characteristics, may be used in place of or in addition to patient data that is sampled from the actual patient bone. In such an instance, a representative bone data set or model may be selected or generated that approximates the lengths and conditions of the actual patient bone. Accordingly, the present disclosure is applicable to all methods of obtaining or generating patient bone data and a patient bone model or a portion thereof.

As shown in FIG. 4 and at step R2 of FIG. 5A, the CT scan or data from the CT scan is segmented and to obtain a three dimensional model 512 of the pelvis 12 and a three dimensional model 514 of the femur 14. At step R3, leg length discrepancy (LLD) is determined prior to the surgery. Determining LLD pre-operatively is described more fully in the subsequent paragraphs.

At steps R4 and R5 of FIG. 5A, the three dimensional models 512, 514 are used by the surgeon to construct a surgical plan at least in part to correct LLD. The surgeon selects an implant at step R4 of FIG. 5A and selects a desired pose (i.e., position and orientation) of the acetabular component and the femoral component relative to the models 512, 514 of the patient's anatomy. For example and as seen in FIG. 4, a planned pose 500 of the acetabular cup can be designated and displayed on a computer display, such as the display device 9. At step R5 of FIG. 5A, the various bone cuts or resections may be determined based upon the desired pose of the implant, among other possible factors.

It is noted that the pre-operatively planning may include a plan for a knee arthroplasty procedure in addition to a hip arthroplasty procedure. The knee arthroplasty procedure may be at the same time as the hip procedure or at a later time. Either way, correction of the LLD, among other deformities, may be in part due to the hip arthroplasty procedure and in part from the knee arthroplasty procedure. For example, the pre-operative planning may include a present correction of a shorter femur in a hip arthroplasty procedure while also planning for an eventual correction to a varus/valgus knee deformity in a knee arthroplasty occurring subsequent to the hip arthroplasty procedure.

A. Leg Length Calculation

In certain instances, LLD may be pre-operatively determined and then compared with an intra-operative determination of LLD, which will be discussed in subsequent sections of this application. In certain instances, step R3 of determining pre-operative LLD may be based on using anatomical information between the proximal femurs and the lower extremities. Through imaging of the pelvis, knees, ankles and feet, the method of determining LLD described herein can be used to acquire information on the mechanical axes and use a distal landmark such as, for example, the calcaneus or talus, among other landmarks, to calculate LLD using the full length of the legs. While conventional (manual surgical) methods typically rely on subjective visual assessments of the knee positions, and conventional computer-assisted surgical methods focus only on "hip length" at the level of the greater or lesser trochanter or above, the method described herein utilizes computer assisted surgical systems and provides an LLD measurement that accounts for the full length of the legs.

Figure 8:
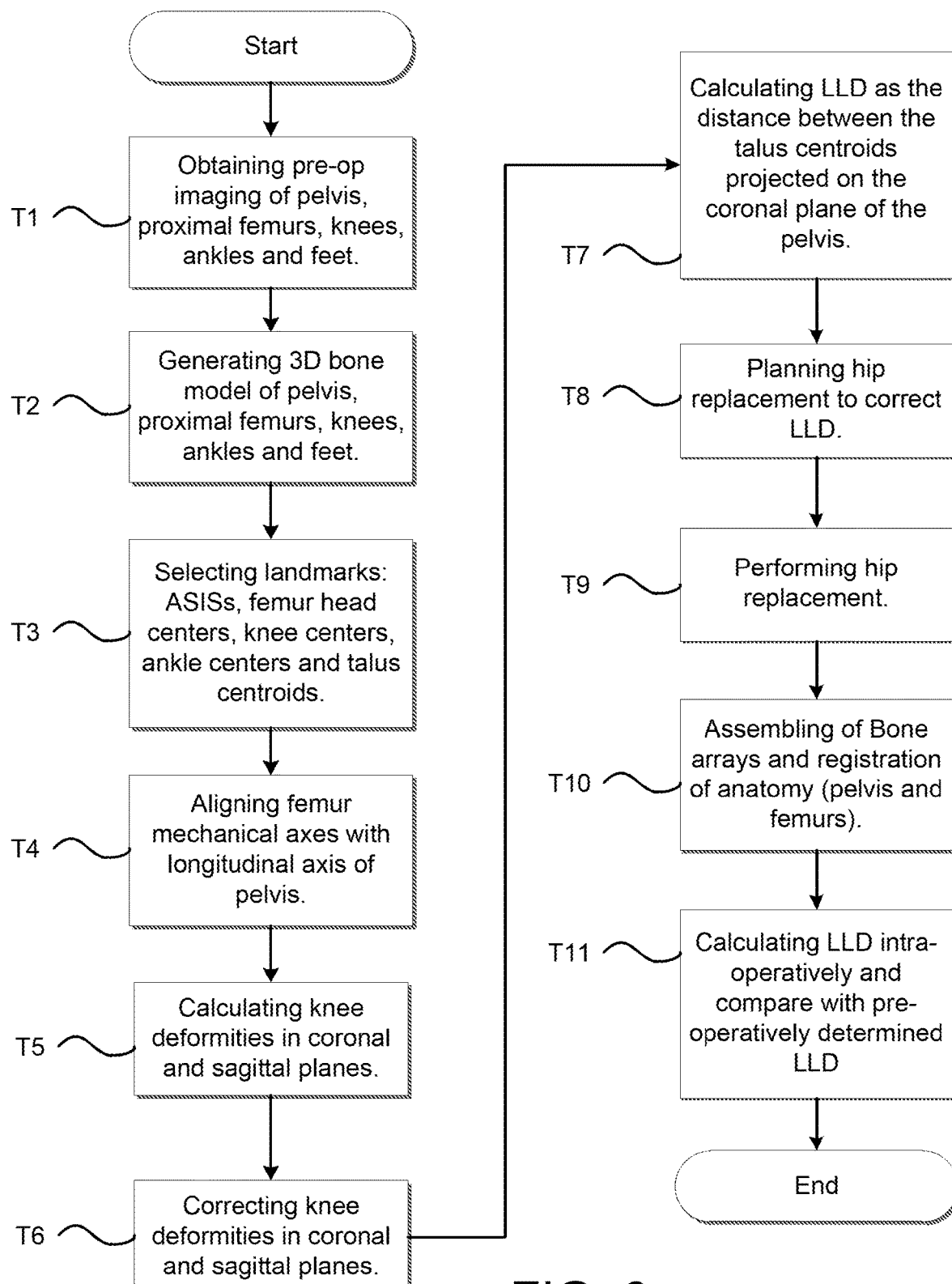
FIG. 8 is a flow chart describing a method for measuring leg length discrepancy pre- and intra-operatively based on lower extremities landmarks.

Referring back to step R1 of FIG. 5A and to step T1 of FIG. 8, which depicts a flow diagram of a method of calculating and correcting LLD, patient bone data or medical images of the pelvis, proximal femur, knee, ankle, and foot may be pre-operatively generated or obtained for both the affected and non-affected legs. As stated previously, various imaging modalities may be utilized to generate the patient bone data such as, for example, CT, MRI, X-ray, or the like. The patient bone data may provide various anatomical landmarks for calculating LLD pre- and intra-operatively.

As shown in step R2 of FIG. 5A and step T2 of FIG. 8, a three-dimensional patient bone model is generated from the patient bone data via a segmentation process or otherwise. In certain instances, a segmentation process may include outlining or segmenting a boundary of a particular bone on each of a plurality of image scans or slices in a certain plane (e.g., sagittal, transverse, coronal). The segmenting of the image scans provides an outline of points on the bone at discrete increments. The plurality of image scans may be positioned adjacent to each other such that there is a gap between each image scan that is equal to the scan spacing (e.g., 2 mm) of the imaging machine. Generating the bone model entails extrapolating a surface in the gap area between the adjacent image slices so as to make a solid or surface model from the plurality of spaced-apart and segmented image scans. While a segmentation process is described herein, any known method of generating the bone models may be used for the purposes of this discussion.

At step T3 of FIG. 8, landmarks are selected in either the medical images or the three dimensional patient bone models. More particularly, the following anatomical landmarks may be selected or identified for each leg: anterior-superior iliac spine (ASIS), femoral head center, knee center, talus centroid. The list of landmarks is not exhaustive and may include additional or different landmarks without departing from the scope of the present disclosure.

Figure 9:
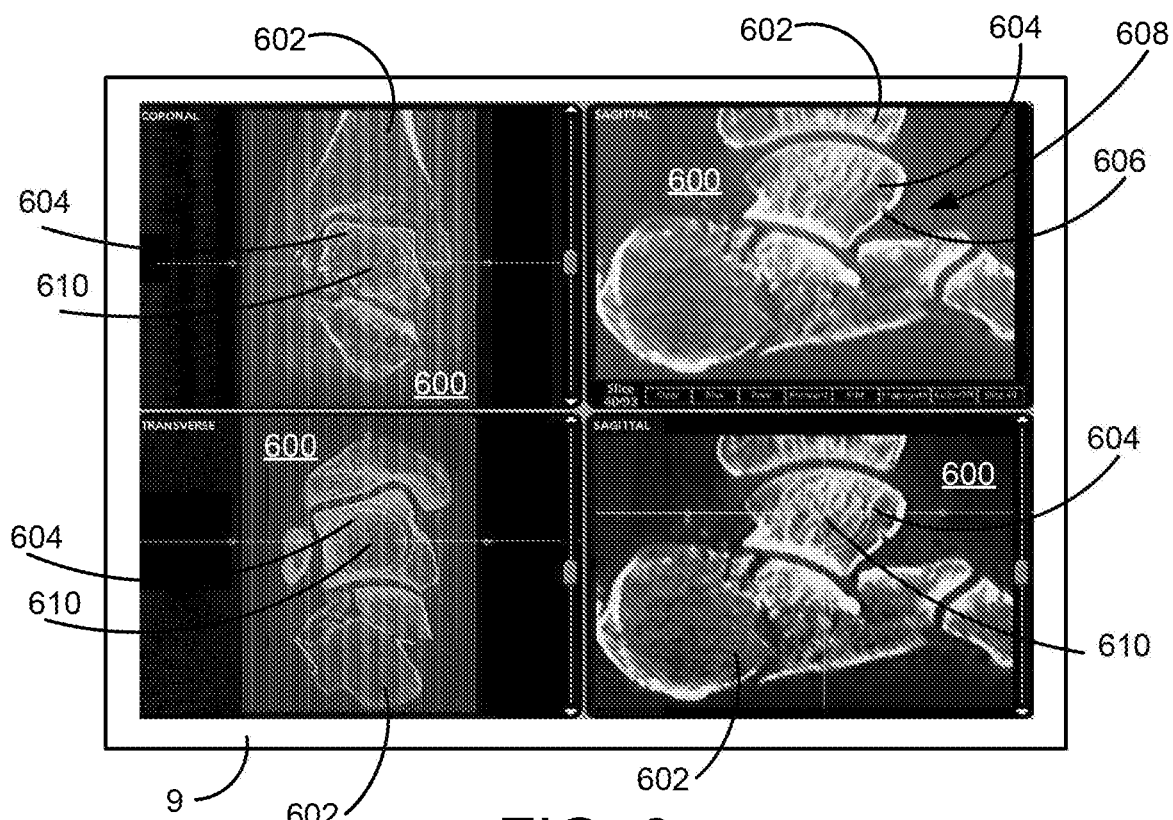
FIG. 9 is a front view of a user interface showing segmentation of the talus bone.
Figure 10:
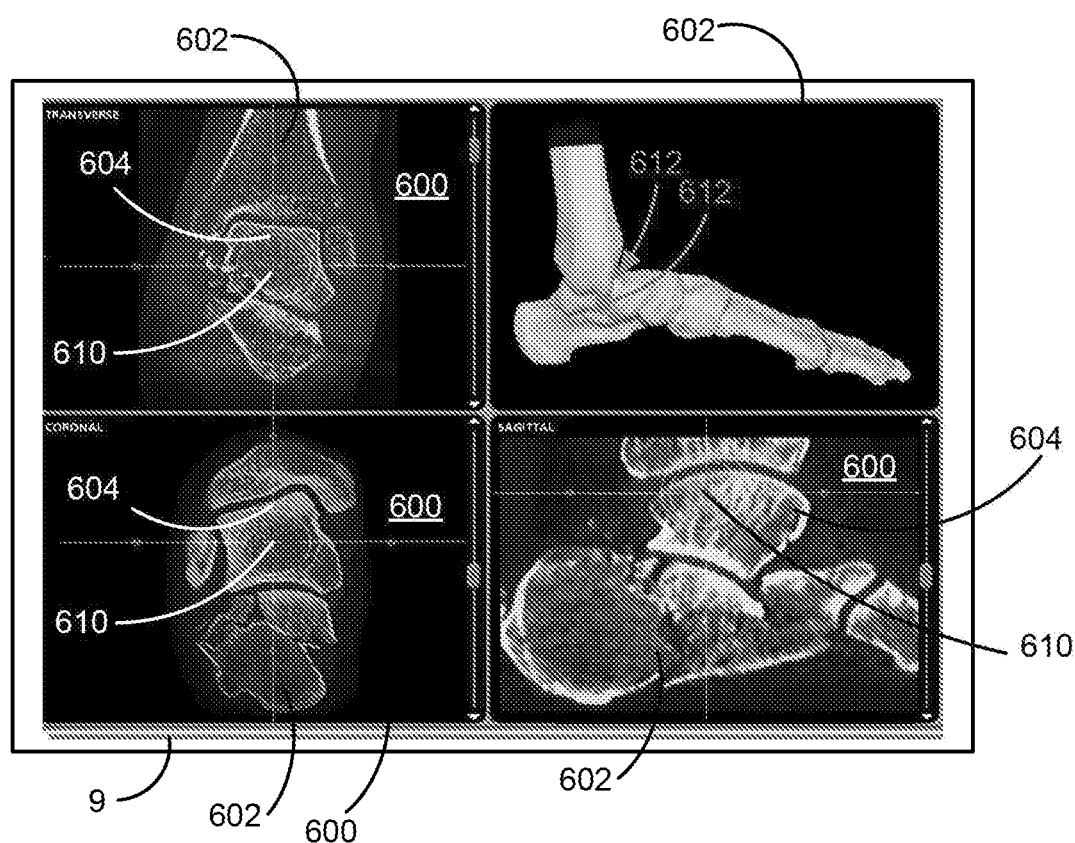
FIG. 10 is a front view of a user interface showing acquisition of the talus bone in a CT image.

An illustrative example of identifying and selecting the talus centroid can be seen in FIGS. 9 and 10. As seen in FIG. 9, which is a display screen 9 illustrating patient bone data 600 in the form of two dimensional images of a patient's foot 602 in various planes, the talus bone 604 is segmented in the top-right image along a bone boundary line 606 that separates the bone 604 from the surrounding tissue 608. A user may segment the individual slices of the talus bone 604, for example, in this view. The views of the talus bone 604 on the top-left, bottom-left, and bottom-right illustrate coronal, transverse, and sagittal views, respectively, and each view illustrates a user selecting a center point 610 of the talus bone 604 with cross-hairs movable via a cursor, for example. Since the talus bone 604 is three-dimensional in physical space, the centroid or center of mass 612, as seen in FIG. 10, may be determined by identifying the center point 610 in the coronal, transverse, and sagittal views of the two dimensional images 602, as shown in FIG. 9.

Upon completing the segmentation process for the talus bone 604 as shown in FIG. 9, the system 5 may generate the three dimensional bone model 614 of the talus bone 604, as well as other segmented bones of the foot, as seen in the top-right of FIG. 10. As seen in the top-left, bottom-right, and bottom-left views of FIG. 10, the illustrations are the same as those shown in FIG. 9. Locational information pertaining to the position of the centroid 612 may be stored within the three dimensional bone model 614.

In certain instances, calculating LLD may be done without generating three dimensional bone models of the various bones described herein. That is, the anatomical landmarks may be identified in the image data (e.g., CT, MRI, X-ray), and coordinates (e.g., x, y, z) associated with the identified landmarks may be used for calculating LLD without generating a 3D surface model of the bones.

And while the talus bone 604 is referenced herein as a distal or lower extremity landmark, other bones at or near the foot (e.g., navicular, calcaneus) or other landmarks of the talus (e.g., most distal aspect of the talus) may be used for purposes of calculating LLD without departing from the teachings of the present disclosure.

While segmentation and identification of landmarks is only shown for the talus bone 604, segmentation and three dimensional bone model generation may continue for the each of the two dimensional images of the pelvis 12, femur 14, and tibia 13, as described in any of the applications incorporated by reference. In certain embodiments, the anatomical landmarks may be selected or identified in the two dimensional medical images or the three dimensional bone model for the femur head centers and knee centers, as shown at step T3 of FIG. 8, in a similar manner as described with reference to the talus bone 604 in FIGS. 9 and 10.

Figures 11A, 11B:
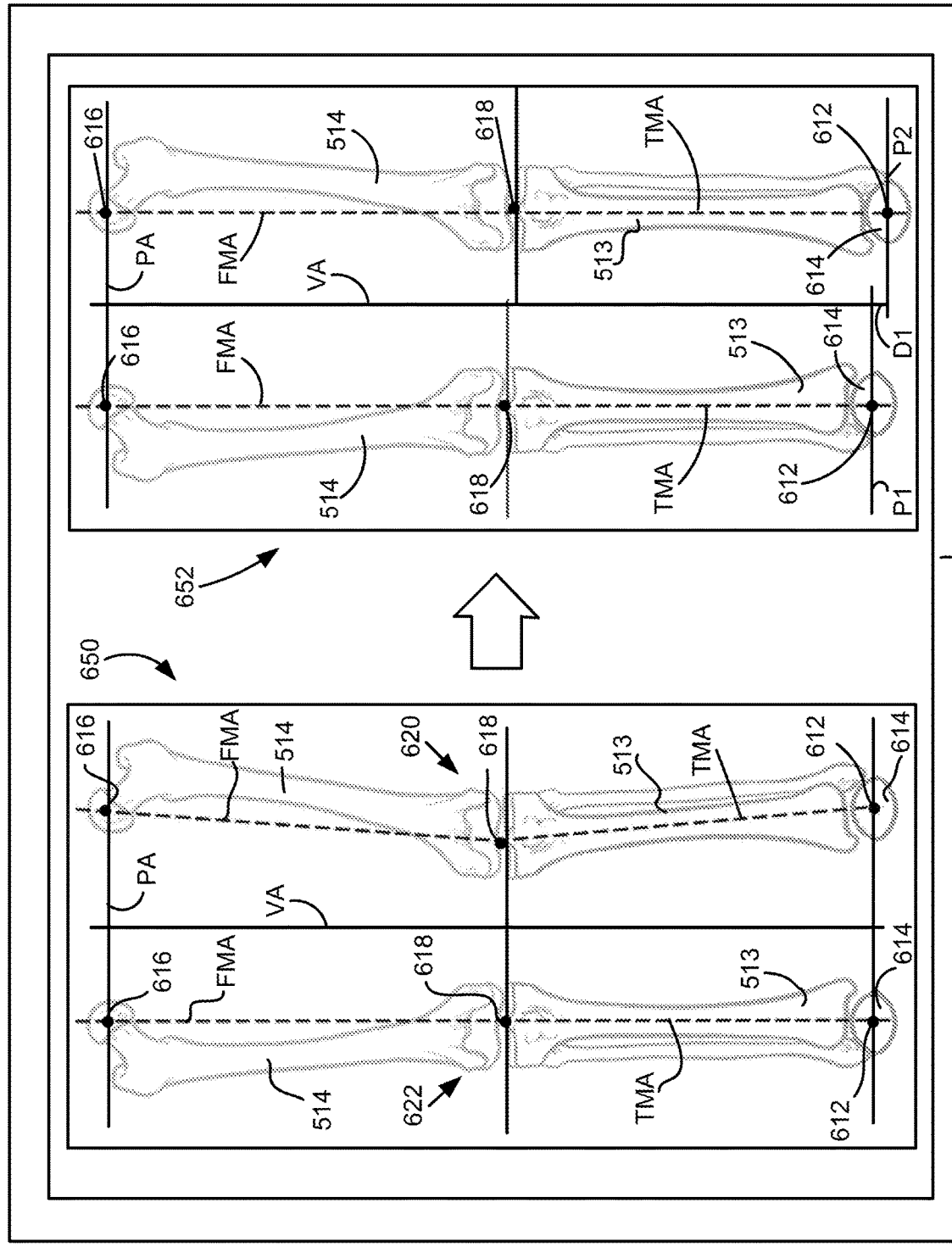
FIG. 11A is a front view of a user interface showing the alignment of the knees in the coronal plane in an un-adjusted manner.
FIG. 11B is a front view of a user interface showing the alignment of the knees in the coronal plane in an adjusted manner.

At step T4 of FIG. 8, the three dimensional bone models of the femur, tibia, and talus 514, 513, 614, together referred to as a patient bone model in an unadjusted state 650 and an adjusted state 652, are displayed on a display screen 9 and the femoral models 514 of the patient bone models 650, 652 are aligned relative to a longitudinal or vertical axis VA of the pelvis, as seen in FIG. 11A. In certain instances, as seen in FIG. 11D, the three dimensional bone model of the pelvis 624 may be used in the calculation and may be used to define a pelvic axis PA, for example, as extending medial-lateral across opposite points on the pelvis. The pelvic axis PA may be used to define the longitudinal or vertical axis VA of the pelvis as being a normal vector of the pelvic axis PA.

In certain instances, the femoral head centers 616 of the right and left femurs of the patient bone models 650, 652 may be parallel to the pelvic axis PA (extending in a medial-lateral direction). In this case, the proximal femurs of the right and left legs are fixed relative to each other such that LLD may be determined at a distal anatomical landmark such as the talus bone, which provides an LLD calculation that encompasses the entire lengths of the legs.

In certain instances, the femoral models 514 may be aligned relative to the vertical axis VA, but not otherwise fixed or "zeroed" relative to each other at the pelvic axis PA (i.e., the right and left femoral head centers may be at different elevations on along the vertical axis VA). While right and left proximal femurs whose femoral head centers 616 are parallel with the pelvic axis PA allows for a length measurement to be determined only by the difference at the distal extremities (as noted by the distance D1 in FIGS. 11B and 11C), the distance D1 may also be found by measuring the entire length of each leg from a proximal landmark (e.g., ASIS, tear-drop, inferior ischial, femoral head center) to a distal landmark (e.g., talus centroid, distal aspect of talus or tibia), and determining the difference in length D1 between the right and left legs. In this way, the proximal landmarks may be at different elevations on the vertical axis VA (i.e., not parallel to the pelvic axis) and a measure of LLD may be found. While the disclosure includes reference to a determination of leg length between the distal landmarks of a right and left leg, other measurements may be used, such as those described in this paragraph and others, to measure the difference in leg length between the right and left legs.

In certain instances and as seen in FIG. 11D, the pelvic model 624 may be used to define the coordinate system of the pelvic axis PA and the longitudinal or vertical axis VA, and the other bone models (e.g., femur, tibia, talus) may be oriented relative to the pelvic model 624. In such instances, the pelvic axis PA may be defined by identifying and selecting opposite points on the pelvic model 624 and defining an axis through the points. For example and as shown in FIG. 11D, the ASIS 625 may be selected (at step T3 of FIG. 8) on a right and left side of the pelvic model 624, and a line (the pelvic axis PA) may extend through the right and left ASIS 625. Once the pelvic axis PA is defined from the pelvic model 624, the longitudinal or vertical axis VA may be defined as a normal vector of the pelvic axis PA.

Once the vertical axis VA is defined, the femoral mechanical axes FMA of the femur models 514 may be aligned with the vertical axis VA of the pelvis, at step T4 of FIG. 8. It is noted, the femur and pelvic models 514, 624 may be joined together such that aligning of the pelvic model 624 with the pelvic axis PA may cause the femur models 514 to move accordingly within the coordinate system. For example, the center of the acetabulum may be used as a common point between the pelvic and femur models 624, 514 to join the models relative to each other, while allowing the femur model 514 to rotate about the center of acetabulum. In this way, once the pelvic model 624 is aligned relative to the pelvic axis PA, the femur model 514 is free to rotate about the center of acetabulum, but is restricted from translating within the coordinate system.

Aligning the pelvic model 624 in the medial-lateral direction via the selected points on, for example, the ASIS and defining the pelvic axis PA in this way allows for consideration of cartilage degeneration, and other factors, at the hip joint that may cause a perceived discrepancy in leg length even if the length of the right and left legs are the same. For example, a right hip joint of a patient may be normal with a healthy amount of cartilage at the joint and a left hip joint may be diseased with very little cartilage present in the joint. The patient may perceive a shorter left leg because of the difference in cartilage at the left hip joint despite the right and left legs being the same length. In such an instance, if femoral points were used to define the pelvic axis PA, as opposed to points on the pelvic model 624, the right and left legs may measure as equal when, in this example, there is degeneration at the joint that causes a perception of leg length discrepancy.

Referring back to FIGS. 11A-11C, while the pelvic model 624 is not displayed, the femoral head centers 616 are shown relative to a pelvic axis PA that may be defined based on selected points (e.g., ASIS) on the pelvic model 624. As seen in FIG. 11A, other deformities, such as those at the knee (e.g., varus/valgus deformities), may remain unadjusted at this point. Adjustment of the knee deformities, for example via a knee arthroplasty and its effect on LLD, will be addressed subsequently.

Upon defining the pelvic axis PA and longitudinal or vertical axis VA, described previously, the mechanical axes of the femur models 514 of the affected (right side) and unaffected side (left side) are aligned to be parallel with the vertical axis VA, as described in step T4 of FIG. 8 and as seen in FIGS. 11A and 11B. Adjustment of the femoral and tibial mechanical axes can be seen in FIG. 11B, which illustrates a display screen 9 showing an adjusted bone model 652, with adjustments made at the hip and knee region. The bone models 650, 652 both include the femur, tibia, and talus bone models 514, 513, 614 and the identified femoral head centers 616, knee centers 618, and talus centroids 612. The femoral mechanical axis FMA is defined between the femoral head center 616 and the knee center 618. The tibial mechanical axis TMA is defined between the knee center 618 and the talus centroid 612.

As seen in FIG. 11A, the un-adjusted bone model 650 represents a valgus knee 620 on the right and a normal knee 622 on the left. The mechanical axes FMA, TMA of the valgus knee 620 are offset and non-parallel to each other and to the vertical axis VA, whereas the mechanical axes FMA, TMA of the normal knee 622 are generally parallel to each other and the vertical axis VA. Upon aligning the femoral mechanical axes FMA with the vertical axis, the bone model 652 will appear as shown in FIG. 11B (which also shows a correction of the valgus knee joint).

In certain instances, the system 5 may use the identified anatomical landmarks as end points associated with the femoral and tibial mechanical axes FMA, TMA, and the system 5 may display the bone models of the femur, tibia, and talus bones 514, 513, 614 in the same orientation as the patient was positioned during an image scan (e.g., CT). In certain instances, an adjustment of the right and left femur models may cause the tibia and talus models to move accordingly while maintaining their original orientation relative to the femur models. In this way, a knee deformity may not be corrected by the initial adjustment of the right and left femur models to be parallel to the vertical axis. In certain instances, the system or surgeon may correct or adjust the orientation of the tibia and talus models relative to the femur so as to correct or adjust a knee or ankle deformity.

At steps T5 and T6 of FIG. 8, the femoral and tibial mechanical axes FMA, TMA, among other parameters including varus/valgus deformities, flexion/extension angles of the knee, among others, can be identified, and adjusted or fixed by the system 5 and displayed on the display screen 9.

The surgeon may view the bone model 650 in FIG. 11A in various views to calculate knee deformities, as seen in step T5 of FIG. 8. For example, varus/valgus deformities may be seen in a coronal view, as depicted in FIG. 11A, whereas flexion/extension angles may be seen in a sagittal view (not shown).

At step T6 and as seen in FIG. 11B, the system 5 may allow a user (e.g., surgeon) to set values for the femoral and tibial mechanical axes FMA, TMA relative to each other or the vertical axis VA to correct varus/valgus deformities, flexion/extension of the knee, and other parameters, such that the three dimensional bone models of the femur, tibia, and talus 514, 513, 614 will be moved according to the inputted values. In this way, the surgeon may virtually align both the affected (right side in FIG. 11A) and non-affected (left side in FIG. 11A) sides of the patient's body in a similar manner (e.g., with both affected and non-affected sides having zero degrees mechanical axis) so LLD may be pre-operatively determined or calculated, regardless of the orientation of the patient's body during the acquisition of two dimensional images.

Thus, as seen in FIG. 11B, the system 5 has adjusted the formerly valgus knee 620 by aligning the femoral and tibial mechanical axes FMA, TMA to be generally parallel with each other and the vertical axis VA. In this way, both knees 620, 622 match each other with regard to femoral and tibial mechanical axes FMA, TMA. Adjustment of the valgus knee may be in anticipation of a knee arthroplasty procedure at the same time as the hip procedure or at another time as part of an effort to correct LLD at the hip and knee.

Figure 11C:
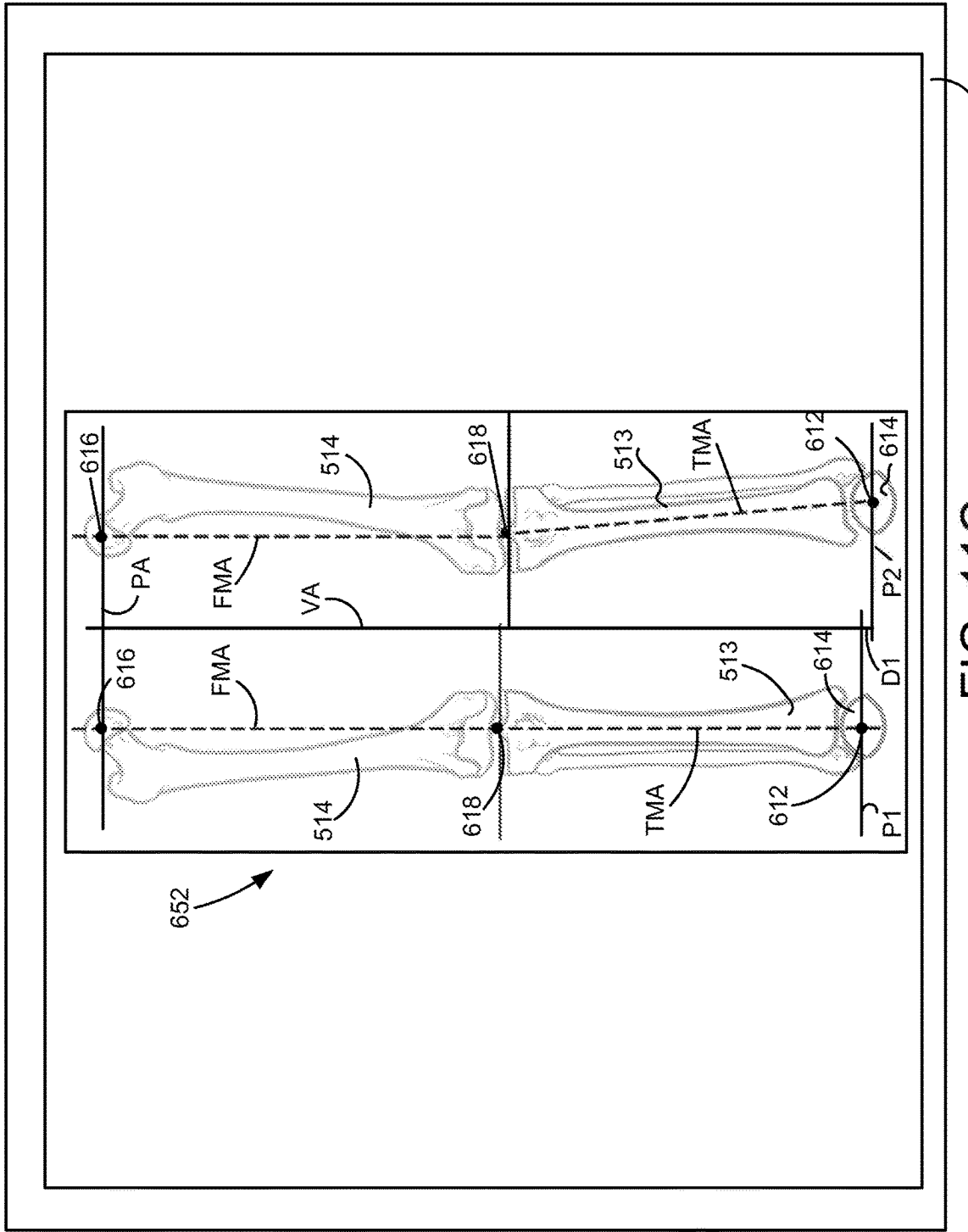
FIG. 11C is another front view of a user interface showing the alignment of the knees in the coronal plane in an adjusted manner.
Figure 11D:
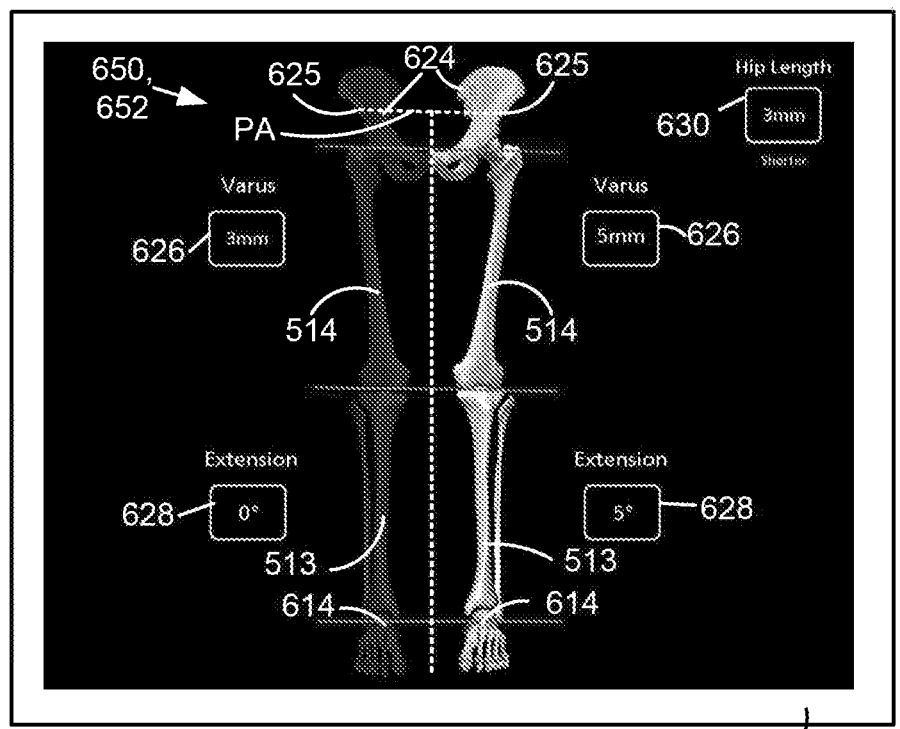
FIG. 11D is a front view of a user interface showing the alignment of the knees in the coronal and sagittal planes.

In certain instances, as seen in FIG. 11C, which is a coronal view of an adjusted bone model 652 displayed on a display screen 9, a surgeon may not adjust the valgus knee on the right, but, upon adjusting the mechanical axis FMA of the femur model 514 to be parallel with the vertical axis VA, the surgeon may leave the orientation of the femur relative to the tibia unadjusted.

In certain instances, as seen in step T7 of FIG. 8, the system 5 may pre-operatively calculate LLD as the distance D1 between the talus centroids 612 as measured relative to the vertical axis VA. More particularly and as seen in FIGS. 11B and 11C, LLD may be measured as the distance D1, along the vertical axis VA, between a first perpendicular line P1 intersecting a first talus centroid 612 and a second perpendicular line P2 intersecting a second talus centroid 612. As discussed previously, the distance D1 may be calculated by measuring the length of the entire right and left legs and calculating the difference. For example, each of the right and left legs may be measured from the pelvic axis (e.g., right and left ASIS) to the talus centroid 612, and the difference between the right and left legs will yield the distance D1.

In this way, an LLD calculation is made by virtually aligning the bone models 650, 652 that will be representative of the patient's physical body following a hip and/or a knee arthroplasty procedure. Using a distal anatomical landmark such as the talus bone provides an LLD calculation that encompasses the entire lengths of the legs as opposed to conventional methods, which focus on only the proximal femur. And by including information from the pelvis, such as using the pelvic axis PA as defined through points (e.g., ASIS) on the pelvis, allows for an LLD calculation that captures potential degeneration at the joint as well as other deformities of the leg(s).

It is also noted that while the embodiment in FIGS. 11A-11C do not show the pelvic model 624, in certain instances, as seen in FIG. 11D, a three dimensional bone model 624 of the pelvis 12 may be depicted on the display screen 9 along with the bone models of the femur, tibia, and talus 514, 513, 614. As seen in FIG. 11D, which is a front view of a display screen 9 showing the bone models 514, 513, 614, a surgeon may set values for varus deformities 626 and extension 628 at the knee. Upon setting the values, the hip length or LLD is displayed 630 accordingly. In the embodiment in FIG. 11D, the un-adjusted bone model 650 and adjusted bone model 652 may be combined to show only a single bone model 650, 652 that is adjusted according to the set values or not adjusted if the values are unmodified.

At step T9 of FIG. 8, the surgeon pre-operatively plans the hip replacement procedure to correct the LLD as determined from step T7. During this step, the surgeon may select an implant and determine the position and orientation of the implant to correct the LLD, as seen in step R4 of FIG. 5A. Selection of the implant and determination of the pose of the implant may influence the determination of the bone cuts or resections to perform on the bones (e.g., proximal femur, acetabulum), as seen in step R5 of FIG. 5A. For example, implant stem length may be a factor to consider to lengthen or shorten the length of the femur to compensate for a particular LLD deformity.

It is noted that in certain instances, patient data may be captured via a localizer tool (e.g., digitizer, navigated ultrasound probe) by a surgeon just prior to or during the surgical procedure. In such instances, the patient data obtained from the localizer tool may take the place of obtaining pre-operative images (e.g., CT, MRI, X-ray) at step T1, of FIG. 8, and generating a 3D bone model at step T2, also of FIG. 8. The localizer tool may gather information about a particular bone such as surface contour information, rotational information (e.g., center of rotation), or location data associated with certain anatomical landmarks. The gathered information may be used by the system 5 to calculate mechanical axes (e.g., FMA, TMA) and develop a model with which to calculate and adjust deformities, at step T5 and T6 of FIG. 8.

The remaining portions of the intra-operative procedure will be discussed in the following sections.

IV. Intra-Operative Procedures

During the surgical procedure and referring back to FIG. 3A, motion of the patient's anatomy and the surgical tool in physical space are tracked by the tracking device 8, and these tracked objects are registered to corresponding models in the navigation system 7 (image space). As a result, objects in physical space are correlated to corresponding models in image space. Therefore, the surgical system 5 knows the actual position of the surgical tool relative to the patient's anatomy and the planned pose 500 (as seen in FIG. 4), and this information is graphically displayed on the display device 9 during the surgical procedure.

A. Tracking and Registration of Femur

Figure 5B:
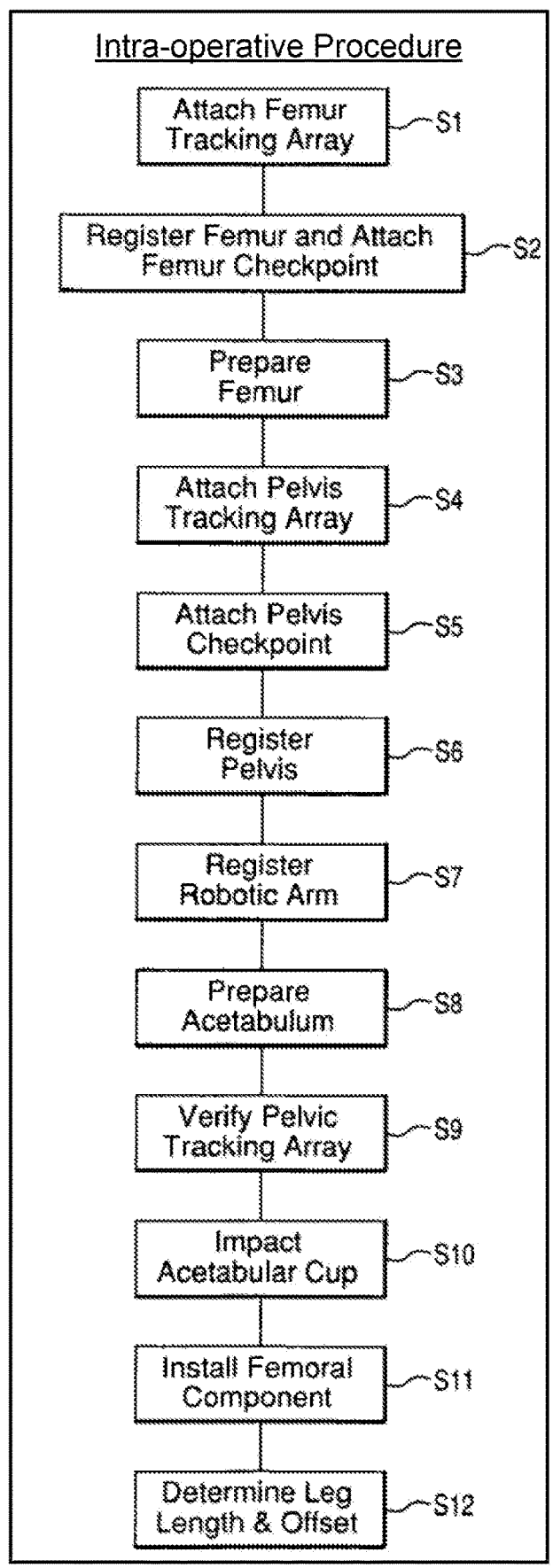
FIG. 5B illustrates an embodiment of steps of intra-operatively performing a hip replacement procedure.

FIG. 5B illustrates an embodiment of intra-operative steps of performing a total hip replacement. In this embodiment, steps S1-S12 may be performed with or without the robotic arm 30. For example, step S8 (reaming) can be performed using robotic arm 30 with the end effector 40 coupled to the operating member 100 or the operating member 200, and step S10 (impacting) can be performed using the robotic arm 30 with the end effector 40 coupled to the operating member 300 or the operating member 400.

In step S1 of the surgical procedure, as seen in FIG. 12A, which is a coronal view of a patient's skeletal structure to undergo a hip arthroplasty procedure, a cortical tracking array 632 is attached to the femur 14 to enable the tracking device 8 to track motion of the femur 14. In step S2, the femur 14 is registered (using any known registration technique) to correlate the pose of the femur 14 (physical space) with the three dimensional model 514 of the femur 14 in the navigation system 7 (image space). Additionally, the femur checkpoint is attached. In step S3, the femur 14 is prepared to receive a femoral implant (e.g., the femoral component 26) using a navigated femoral broach.

B. Tracking and Registration of Pelvis

In step S4 of FIG. 5B, a pelvic tracking array 634 is attached to the pelvis 12 to enable the tracking device 8 to track motion of the pelvis 12, as seen in FIG. 12A. In step S5, a checkpoint is attached to the pelvis 12 for use during the surgical procedure to verify that the pelvic tracking array has not moved in relation to the pelvis 12. The checkpoint can be, for example, a checkpoint as described in U.S. patent application Ser. No. 11/750,807 (Pub. No. US 2008/0004633), filed May 18, 2007, and hereby incorporated by reference herein in its entirety.

Figure 6:
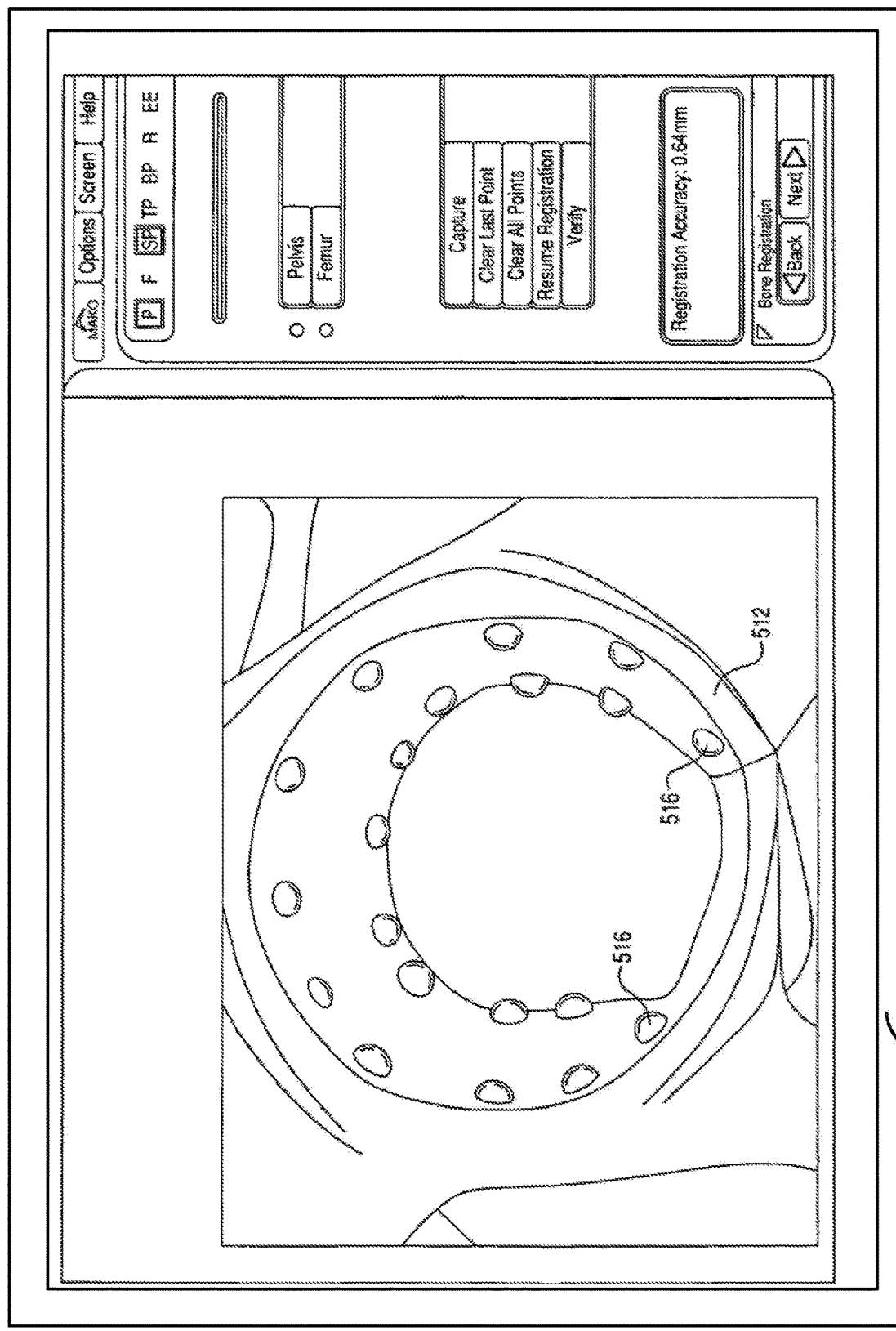
FIGS. 6 and 7 illustrate an embodiment of a pelvic registration method shown on a display screen.

In step S6, the pelvis 12 is registered to correlate the pose of the pelvis 12 (physical space) with the three dimensional model 512 of the pelvis 12 in the navigation system 7 (image space). In certain embodiments, as shown in FIG. 6, registration is accomplished using the tracked navigation probe 56 to collect points on the pelvis 12 (physical space) that are then matched to corresponding points on the three dimensional model 512 of the pelvis 12 (image space). Two methods of registering the three dimensional model 512 of the pelvis (image space) and the pelvis 12 (physical space) are described in the subsequent sections of this application.

As shown in FIG. 6, the display device 9 may show the representation 512 of the pelvis 12, including one or more registration points 516. The registration points 516 help the surgeon understand where on the actual anatomy to collect points with the tracked probe. The registration points 516 can be color coded to further aid the surgeon. For example, a registration point 516 on the pelvis 12 to be collected next with the tracked probe can be colored yellow, while registration points 516 that have already been collected can be colored green and registration points 516 that will be subsequently collected can be colored red. After registration, the display device 9 can show the surgeon how well the registration algorithm fit the physically collected points to the representation 512 of the pelvis 12.

Figure 7:
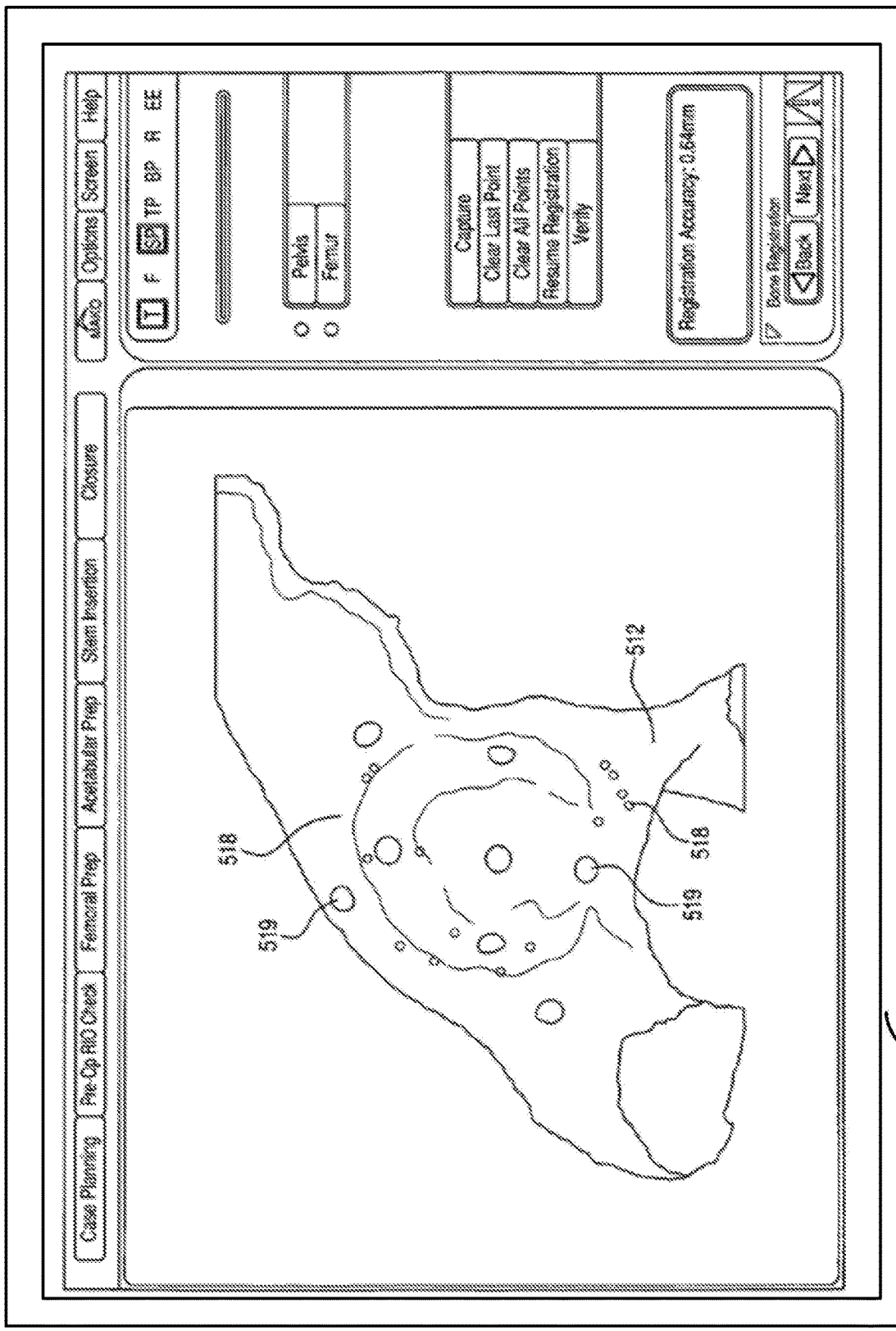

For example, as shown in FIG. 7, error points 518 can be displayed to illustrate how much error exists in the registration between the surface of the representation 512 and the corresponding surface of the physical pelvis 12. In one embodiment, the error points 518 can be color coded, for example, with error points 518 representing minimal error displayed in green and error points 518 representing increasing amounts of error displayed in blue, yellow, and red. As an alternative to color coding, error points 518 representing different degrees of error could have different shapes or sizes. Verification points 519 can also be displayed. The verification points 519 illustrate to the surgeon where to collect points with the tracked probe to verify the registration. When a registration point 519 is collected, the software of the navigation system 7 displays the error (e.g., numerically in millimeters) between the actual point collected on the anatomy and the registered location of the representation 512 in physical space. If the registration error is too high, the surgeon re-registers the pelvis 12 by repeating the registration process of step S6.

C. Registering of Robotic Arm

Referring back to FIG. 5B, after registering the pelvis at step S6, the robotic arm 30 may be registered at step S7. In this step, the robotic arm 30 is registered to correlate the pose of the robotic arm 30 (physical space) with the navigation system 7 (image space). The robotic arm 30 can be registered, for example, as described in U.S. patent application Ser. No. 11/357,197 (Pub. No. US 2006/0142657), filed Feb. 21, 2006, and hereby incorporated by reference herein in its entirety.

D. Preparation of the Acetabulum and Performance of the Surgical Procedure

In operation, the surgeon can use the robotic arm 30 to facilitate a joint replacement procedure, such as reaming bone and implanting an acetabular cup for a total hip replacement or hip resurfacing procedure. As explained above, the robotic arm 30 includes a surgical tool configured to be coupled to a cutting element (for reaming) and to engage a prosthetic component (for impacting). For example, for reaming, the end effector 40 can couple to the operating member 100 or the operating member, each of which couples to the cutting element. Similarly, for impacting, the end effector 40 can couple to the operating member or the operating member, each of which engages the prosthetic component. The robotic arm 30 can be used to ensure proper positioning during reaming and impacting.

In step S8 of FIG. 5B, the surgeon resurfaces the acetabulum 22 using a reamer, such as the operating member 100, coupled to the robotic arm 30. As described above in connection with the operating member 100, the surgeon couples the appropriate operating member (e.g., a straight or offset reamer) to the end effector 40, connects the cutting element to the received operating member, and manually manipulates the robotic arm 30 to ream the acetabulum 22. During reaming, the robotic arm 30 provides haptic (force feedback) guidance to the surgeon. The haptic guidance constrains the surgeon's ability to manually move the surgical tool to ensure that the actual bone cuts correspond in shape and location to planned bone cuts (i.e., cuts consistent with the surgical plan).

In step S9 of FIG. 5B, the surgeon verifies that the registration (i.e., the geometric relationship) between the acetabular tracking array and the pelvis 12 is still valid by contacting the pelvis checkpoint with a tracked probe as described, for example, in U.S. patent application Ser. No. 11/750,807 (Pub. No. US 2008/0004633), filed May 18, 2007, and hereby incorporated by reference herein in its entirety. If registration has degraded (e.g., because the acetabular tracking array was bumped during reaming), the pelvis 12 is re-registered. Registration verification can be performed any time the surgeon wants to check the integrity of the acetabular registration.

In step S10 of FIG. 5B, the prosthetic component 316 is implanted on the reamed acetabulum 22 using an impactor tool. In a manner identical to that described above in connection with step S8 (reaming), during the impaction step S10, the display device 9 can show the planned pose 500, the activation region 510, the representations 512, 514 of the anatomy, and a representation of the surgical tool. Also as described above in connection with step S8, if the surgeon moves the end effector 40 to override the haptic feedback, the controller can initiate automatic control of the surgical tool to substantially align at least one aspect of the actual pose with the corresponding desired aspect of the target pose.

E. Leg Length Calculation

In step S11 of FIG. 5B, the surgeon installs the femoral component on the femur 14. Next, in step S12 of FIG. 5B and step T11 of FIG. 8, the surgeon determines leg length and femoral offset. At any time during the surgical procedure, the display device 9 can show data related to progress and/or outcome. For example, after reaming in step S8 and/or impacting in step S10), data relating to the actual position of the reamed acetabulum 22 (or the implanted acetabular cup) can include, for example, numerical data representing error between the actual and planned locations in the three orthogonal planes of the patient's anatomy (i.e., medial/lateral, superior/inferior, and anterior/posterior).

In certain instances, step S12 of FIG. 5B and step T11 of FIG. 8 for determining leg length discrepancy (LLD) may include comparing the pre-operatively determined LLD with an intra-operative measurement of LLD.

In certain instances, intra-operative LLD may be determined by based on the position of the femoral and pelvic tracking arrays 634, 632, as seen in FIGS. 12A and 12B. FIG. 12A depicts a coronal view of a patient's skeletal structure including the pelvis 12, femur 14, and knee joint 10 with a pelvic tracking array 634 positioned in the pelvis 12 and a femoral tracking array 632 positioned in the femur 14 prior to the resection of the proximal femur including the femoral neck and head 18, 16. FIG. 12B depicts a coronal view of a patient's skeletal structure including the pelvis 12, femur 14, and knee joint 10 with a pelvic tracking array 634 positioned in the pelvis 12 and a femoral tracking array 632 positioned in the femur 14 following the resection of the proximal femur and implantation of femoral and acetabular components of a hip implant system 636.

Upon registering the pelvis 12 and the femur 14 via the pelvic tracking array 634 and the femoral tracking array 632, the system 5 may calculate a first value or distance D10 between the tracking arrays 634, 632 in a given pose(s) (i.e., position and orientation) of the femur 14 relative to the pelvis 12. For example, the surgeon may position the patient's femur 14 such that the femoral mechanical axis (not shown in FIG. 12A) is parallel to the vertical axis (not shown in FIG. 12A). In certain instances, the surgeon may use the tracking ability of the system 5 to verify that the femur 14 is positioned in the correct pose relative to the pelvis 12 for determining the distance D20.

Following the hip replacement procedure where the proximal femur is resected and replaced with a femoral component that is positioned within an acetabular component, as seen in FIG. 12B, the surgeon may calculate a second value or distance D20 between the tracking arrays 634, 632 in a given pose(s) of the femur 14 relative to the pelvis 12. In certain instances, the pose may be the same for determining the distances D10, D20.

The difference between the pre-resection distance D10 and the post-resection distance D20 is given by distance D30, as seen in FIG. 12B. The distance D30 represents the change in leg length that resulted from the actual hip replacement procedure. This distance D30 may then be compared with the pre-operatively calculated LLD. In certain instances, where a hip replacement procedure was the only planned procedure (i.e., a knee arthroplasty was not planned for), the post-operative distance D30 may be compared with the pre-operative value of LLD. If, for example, a surgeon desired to correct a knee deformity that pre-operatively showed a 3 mm shorter leg, a post-operative distance D30 change of 3 mm longer, for example, may indicate that the hip replacement procedure was successful in correcting LLD.

In certain instances, where a knee arthroplasty procedure is to take place at a given time after the hip replacement procedure, the distance D30 associated with a change in the proximal femur may be one component of the overall LLD to be fixed. That is, the surgeon may calculate or determine that the hip replacement procedure will fix total LLD by a factor of X, and a subsequent knee replacement procedure (e.g., to fix varus/valgus deformity) will fix total LLD by a factor of Y, where X plus Y equals the total LLD.

Figure 12D:
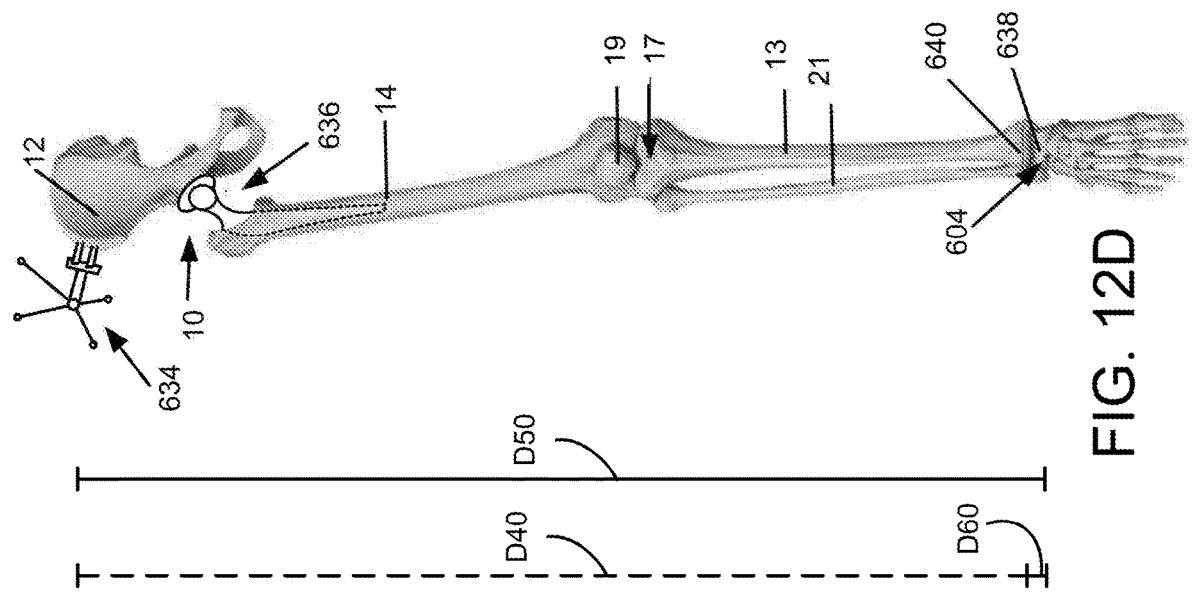
FIG. 12D is a coronal view of a skeletal structure of a patient with a pelvic tracking array in the pelvis and distal extremity points probed via a localizer device following the resection of the femur and implantation of a femoral and acetabular component of a hip replacement system.
Figure 12C:
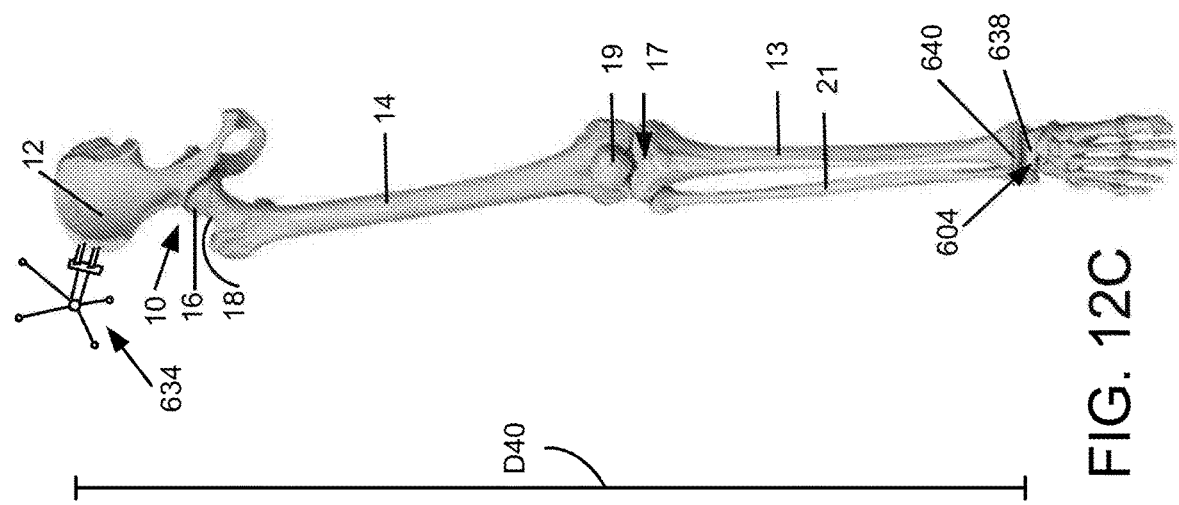
FIG. 12C is a coronal view of a skeletal structure of a patient with a pelvic tracking array in the pelvis and distal extremity points probed via a localizer device prior to resection of the femur.

In certain instances, a pre- and post-resection determination of leg length may be determined without the aid of a femoral tracking array. For example, as seen in FIG. 12C, which is a front view of a right side of a pelvis 12, hip joint 10, femur 14, knee joint 17, patella 19, fibula 21, and talus 604 prior to a hip replacement surgery, a surgeon may calculate a pre-resection LLD as a distance D40 between the pelvic tracking array 634 and a distal landmark such as a distal aspect of the talus 638 or a distal aspect of the tibia 640. As seen in FIG. 12D, which is a front view of a right side of a pelvis 12, hip joint 10, femur 14, knee joint 17, patella 19, fibula 21, and talus 604 following a hip replacement surgery, the surgeon may calculate a post-resection LLD as a distance D50 between the pelvic tracking array 634 and a distal landmark such as a distal aspect of the talus 638 or a distal aspect of the tibia 640.

The difference between the pre-resection distance D40 and the post-resection distance D50 is given by distance D60, as seen in FIG. 12D. The distance D60 represents the change in leg length that resulted from the actual hip replacement procedure. This distance D60 may then be compared with the pre-operatively calculated LLD. In certain instances, where a hip replacement procedure was the only planned procedure (i.e., a knee arthroplasty was not planned for), the post-operative distance D60 may be compared with the pre-operative value of LLD. If, for example, a surgeon desired to correct a knee deformity that pre-operatively showed a 3 mm shorter leg, a post-operative distance D60 change of 3 mm longer, for example, may indicate that the hip replacement procedure was successful in correcting LLD.

In certain instances, where a knee arthroplasty procedure is to take place at a given time after the hip replacement procedure, the distance D60 associated with a change in the proximal femur may be one component of the overall LLD to be fixed. That is, the surgeon may calculate or determine that the hip replacement procedure will fix total LLD by a factor of X, and a subsequent knee replacement procedure (e.g., to fix varus/valgus deformity) will fix total LLD by a factor of Y, where X plus Y equals the total LLD.

Instead of using the femoral tracking array (shown in FIGS. 12A-12B) the distal landmarks may be captured by the surgeon via a digitizer or tracked navigation probe. For example, the surgeon may place the distal tip of a tracked probe against a distal landmark (e.g., distal aspect of tibia 640 or talus 638) and the location of the landmark may be stored by the system 5. In this way, the surgeon may capture or log the location of the distal landmark on the patient's distal extremity pre- and post-hip replacement, and the difference in the distance between the distal extremity and the pelvic tracking array 634 may provide a difference in LLD as a result of the surgical procedure. It is noted that the distal aspects of the tibia and talus 640, 638 are exemplary and other distal landmarks may be similarly employed without departing from the scope of the present disclosure.

V. Example Computing System

Figure 13:
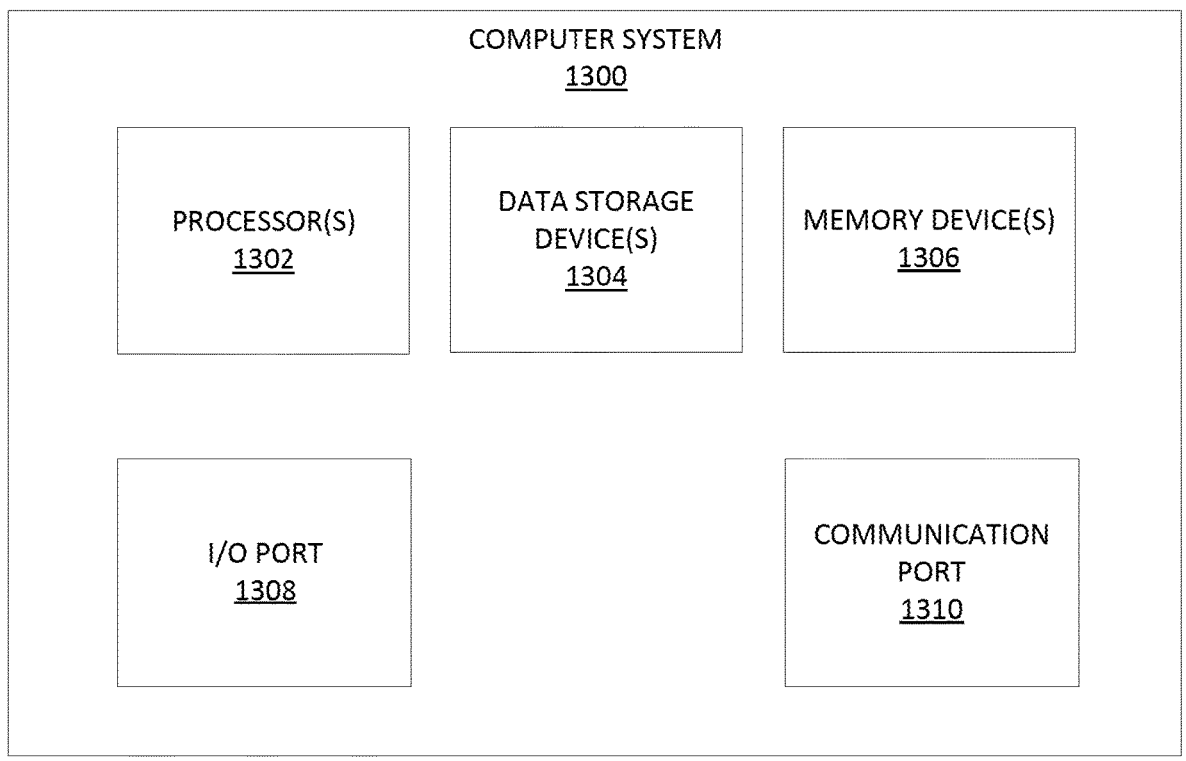
FIG. 13 is an example computing system having one or more computing units that may implement various systems and methods discussed herein is provided.

Referring to FIG. 13, a detailed description of an example computing system 1300 having one or more computing units that may implement various systems and methods discussed herein is provided. The computing system 1300 may be applicable to any of the computers or systems utilized in the preoperative or intra-operative planning of the arthroplasty procedure (e.g., registration, leg length discrepancy), and other computing or network devices. It will be appreciated that specific implementations of these devices may be of differing possible specific computing architectures not all of which are specifically discussed herein but will be understood by those of ordinary skill in the art.

The computer system 1300 may be a computing system that is capable of executing a computer program product to execute a computer process. Data and program files may be input to the computer system 1300, which reads the files and executes the programs therein. Some of the elements of the computer system 1300 are shown in FIG. 13, including one or more hardware processors 1302, one or more data storage devices 1304, one or more memory devices 1308, and/or one or more ports 1308-1310. Additionally, other elements that will be recognized by those skilled in the art may be included in the computing system 1300 but are not explicitly depicted in FIG. 13 or discussed further herein. Various elements of the computer system 1300 may communicate with one another by way of one or more communication buses, point-to-point communication paths, or other communication means not explicitly depicted in FIG. 13.

The processor 1302 may include, for example, a central processing unit (CPU), a microprocessor, a microcontroller, a digital signal processor (DSP), and/or one or more internal levels of cache. There may be one or more processors 1302, such that the processor 1302 comprises a single central-processing unit, or a plurality of processing units capable of executing instructions and performing operations in parallel with each other, commonly referred to as a parallel processing environment.

The computer system 1300 may be a conventional computer, a distributed computer, or any other type of computer, such as one or more external computers made available via a cloud computing architecture. The presently described technology is optionally implemented in software stored on the data stored device(s) 1304, stored on the memory device(s) 1306, and/or communicated via one or more of the ports 1308-1310, thereby transforming the computer system 1300 in FIG. 13 to a special purpose machine for implementing the operations described herein. Examples of the computer system 1300 include personal computers, terminals, workstations, mobile phones, tablets, laptops, personal computers, multimedia consoles, gaming consoles, set top boxes, and the like.

The one or more data storage devices 1304 may include any non-volatile data storage device capable of storing data generated or employed within the computing system 1300, such as computer executable instructions for performing a computer process, which may include instructions of both application programs and an operating system (OS) that manages the various components of the computing system 1300. The data storage devices 1304 may include, without limitation, magnetic disk drives, optical disk drives, solid state drives (SSDs), flash drives, and the like. The data storage devices 1304 may include removable data storage media, non-removable data storage media, and/or external storage devices made available via a wired or wireless network architecture with such computer program products, including one or more database management products, web server products, application server products, and/or other additional software components. Examples of removable data storage media include Compact Disc Read-Only Memory (CD-ROM), Digital Versatile Disc Read-Only Memory (DVD-ROM), magneto-optical disks, flash drives, and the like. Examples of non-removable data storage media include internal magnetic hard disks, SSDs, and the like. The one or more memory devices 1306 may include volatile memory (e.g., dynamic random access memory (DRAM), static random access memory (SRAM), etc.) and/or non-volatile memory (e.g., read-only memory (ROM), flash memory, etc.).

Computer program products containing mechanisms to effectuate the systems and methods in accordance with the presently described technology may reside in the data storage devices 1304 and/or the memory devices 1306, which may be referred to as machine-readable media. It will be appreciated that machine-readable media may include any tangible non-transitory medium that is capable of storing or encoding instructions to perform any one or more of the operations of the present disclosure for execution by a machine or that is capable of storing or encoding data structures and/or modules utilized by or associated with such instructions. Machine-readable media may include a single medium or multiple media (e.g., a centralized or distributed database, and/or associated caches and servers) that store the one or more executable instructions or data structures.

In some implementations, the computer system 1300 includes one or more ports, such as an input/output (I/O) port 1308 and a communication port 1310, for communicating with other computing, network, or vehicle devices. It will be appreciated that the ports 1308-1310 may be combined or separate and that more or fewer ports may be included in the computer system 1300.

The I/O port 1308 may be connected to an I/O device, or other device, by which information is input to or output from the computing system 1300. Such I/O devices may include, without limitation, one or more input devices, output devices, and/or environment transducer devices.

In one implementation, the input devices convert a human-generated signal, such as, human voice, physical movement, physical touch or pressure, and/or the like, into electrical signals as input data into the computing system 1300 via the I/O port 1308. Similarly, the output devices may convert electrical signals received from computing system 1300 via the I/O port 1308 into signals that may be sensed as output by a human, such as sound, light, and/or touch. The input device may be an alphanumeric input device, including alphanumeric and other keys for communicating information and/or command selections to the processor 1302 via the I/O port 1308. The input device may be another type of user input device including, but not limited to: direction and selection control devices, such as a mouse, a trackball, cursor direction keys, a joystick, and/or a wheel; one or more sensors, such as a camera, a microphone, a positional sensor, an orientation sensor, a gravitational sensor, an inertial sensor, and/or an accelerometer; and/or a touch-sensitive display screen ("touchscreen"). The output devices may include, without limitation, a display, a touchscreen, a speaker, a tactile and/or haptic output device, and/or the like. In some implementations, the input device and the output device may be the same device, for example, in the case of a touchscreen.

In one implementation, a communication port 1310 is connected to a network by way of which the computer system 1300 may receive network data useful in executing the methods and systems set out herein as well as transmitting information and network configuration changes determined thereby. Stated differently, the communication port 1310 connects the computer system 1300 to one or more communication interface devices configured to transmit and/or receive information between the computing system 1300 and other devices by way of one or more wired or wireless communication networks or connections. Examples of such networks or connections include, without limitation, Universal Serial Bus (USB), Ethernet, Wi-Fi, Bluetooth®, Near Field Communication (NFC), Long-Term Evolution (LTE), and so on. One or more such communication interface devices may be utilized via the communication port 1310 to communicate one or more other machines, either directly over a point-to-point communication path, over a wide area network (WAN) (e.g., the Internet), over a local area network (LAN), over a cellular (e.g., third generation (3G) or fourth generation (4G)) network, or over another communication means. Further, the communication port 1310 may communicate with an antenna or other link for electromagnetic signal transmission and/or reception.

In an example implementation, patient data, bone models (e.g., generic, patient specific), transformation software, tracking and navigation software, registration software, and other software and other modules and services may be embodied by instructions stored on the data storage devices 1304 and/or the memory devices 1306 and executed by the processor 1302. The computer system 1300 may be integrated with or otherwise form part of the surgical system 100.

The system set forth in FIG. 13 is but one possible example of a computer system that may employ or be configured in accordance with aspects of the present disclosure. It will be appreciated that other non-transitory tangible computer-readable storage media storing computer-executable instructions for implementing the presently disclosed technology on a computing system may be utilized.

In the present disclosure, the methods disclosed herein, for example, those shown in FIGS. 5 and 8, among others, may be implemented as sets of instructions or software readable by a device. Further, it is understood that the specific order or hierarchy of steps in the methods disclosed are instances of example approaches. Based upon design preferences, it is understood that the specific order or hierarchy of steps in the method can be rearranged while remaining within the disclosed subject matter. The accompanying method claims present elements of the various steps in a sample order, and are not necessarily meant to be limited to the specific order or hierarchy presented.

The described disclosure including any of the methods described herein may be provided as a computer program product, or software, that may include a non-transitory machine-readable medium having stored thereon instructions, which may be used to program a computer system (or other electronic devices) to perform a process according to the present disclosure. A machine-readable medium includes any mechanism for storing information in a form (e.g., software, processing application) readable by a machine (e.g., a computer). The machine-readable medium may include, but is not limited to, magnetic storage medium, optical storage medium; magneto-optical storage medium, read only memory (ROM); random access memory (RAM); erasable programmable memory (e.g., EPROM and EEPROM); flash memory; or other types of medium suitable for storing electronic instructions.

While the present disclosure has been described with reference to various implementations, it will be understood that these implementations are illustrative and that the scope of the present disclosure is not limited to them. Many variations, modifications, additions, and improvements are possible. More generally, embodiments in accordance with the present disclosure have been described in the context of particular implementations. Functionality may be separated or combined in blocks differently in various embodiments of the disclosure or described with different terminology. These and other variations, modifications, additions, and improvements may fall within the scope of the disclosure as defined in the claims that follow.

In general, while the embodiments described herein have been described with reference to particular embodiments, modifications can be made thereto without departing from the spirit and scope of the disclosure. Note also that the term "including" as used herein is intended to be inclusive, i.e. "including but not limited to."

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

We claim:

1. A computer program stored on one or more tangible, non-transitory, computer-readable storage media having executable instructions for performing the computer program on a computing system, the computer program comprising:

receiving patient bone data having a first side and a second side, one of the first or second sides including a degenerate or deformed condition;

generating a computer model of the first and second sides from the patient bone data;

identifying anatomical landmarks in the patient bone data or the computer model, the anatomical landmarks comprising: a first proximal point and a first distal point on the first side; and a second proximal point and a second distal point on the second side;

orienting the first and second sides of the computer model relative to each other in a coordinate system such that: a pelvic axis extending through the first and second proximal points are generally perpendicular to a longitudinal axis of the first and second sides of the computer model; and a first axis associated with a first femur and a second axis associated with a second femur are generally parallel to the longitudinal axis;

calculating a leg length discrepancy based on the first and second sides of the computer model after orienting the first and second sides of the computer model relative to each other.

2. The computer program of claim 1, wherein the first proximal point corresponds to a femoral head center of a first femur of the first side of the patient bone data, and the second proximal point corresponds to a femoral head center of a second femur of the second side of the patient bone data.

3. The computer program of claim 1, wherein the first distal point corresponds to a first point in or on a first bone in a first foot region of the first side of the patient bone data, and the second distal point corresponds to a second point in or on a second bone in a second foot region of the second side of the patient bone data.

4. The computer program of claim 1, further comprising: adjusting an orientation of at least one of a first knee joint of the computer model defined between a first femur and a first tibia of the first side of the patient bone data or a second knee joint of the computer model defined between a second femur and a second tibia of the second side of the patient bone data.

5. The computer program of claim 1, wherein the patient bone data comprises at least one of CT images, MR images, or X-ray images.

6. The computer program of claim 1, wherein the leg length discrepancy comprises determining a distance between the first and second distal points in a direction of the longitudinal axis.

7. The computer program of claim 1, wherein the leg length discrepancy comprises determining a difference between a first distance and a second distance, the first distance defined between the first proximal point and the first distal point on the first side, the second distance defined between the second proximal point and the second distal point on the second side.

* * * * *